(12) United States Patent
Neubardt

(10) Patent No.: US 9,042,960 B2
(45) Date of Patent: May 26, 2015

(54) DETERMINING AND PLACING SPINAL IMPLANTS OR PROSTHESES

(71) Applicant: Seth L. Neubardt, Mamaroneck, NY (US)

(72) Inventor: Seth L. Neubardt, Mamaroneck, NY (US)

( * ) Notice: Subject to any disclaimer, the term of this patent is extended or adjusted under 35 U.S.C. 154(b) by 0 days.

(21) Appl. No.: 14/180,495

(22) Filed: Feb. 14, 2014

(65) Prior Publication Data

US 2014/0163573 A1 Jun. 12, 2014

Related U.S. Application Data

(60) Division of application No. 12/898,871, filed on Oct. 6, 2010, now abandoned, which is a continuation-in-part of application No. 12/215,097, filed on Jun. 25, 2008, now abandoned.

(60) Provisional application No. 60/937,055, filed on Jun. 25, 2007.

(51) Int. Cl.
| | |
|---|---|
| *A61B 5/05* | (2006.01) |
| *A61B 6/00* | (2006.01) |
| *A61F 2/46* | (2006.01) |
| *A61B 5/107* | (2006.01) |
| *A61B 17/88* | (2006.01) |
| *A61B 5/055* | (2006.01) |
| *A61B 5/00* | (2006.01) |

(Continued)

(52) U.S. Cl.
CPC .............. *A61F 2/4657* (2013.01); *A61B 5/055* (2013.01); *A61B 5/1077* (2013.01); *A61B 5/4504* (2013.01); *A61B 5/4514* (2013.01); *A61B 5/4561* (2013.01); *A61B 6/505* (2013.01); *A61B 19/24* (2013.01); *A61B 19/46* (2013.01); *A61B 19/50* (2013.01); *A61B 2017/0256* (2013.01); *A61B 2019/502* (2013.01); *A61B 2019/504* (2013.01); *A61B 2019/505* (2013.01); *A61B 2019/508* (2013.01); *A61B 2019/5236* (2013.01); *A61B 2019/5238* (2013.01); *A61F 2/44* (2013.01); *A61F 2/441* (2013.01); *A61F 2/442* (2013.01); *A61F 2002/3008* (2013.01); *A61F 2002/302* (2013.01); *A61F 2002/30583* (2013.01); *A61F 2002/30586* (2013.01); *A61F 2002/30841* (2013.01); *A61F 2002/30952* (2013.01); *A61F 2210/0085* (2013.01); *A61F 2230/0065* (2013.01); *A61F 2250/0098* (2013.01); *A61B 17/8855* (2013.01)

(58) Field of Classification Search
None
See application file for complete search history.

(56) References Cited

U.S. PATENT DOCUMENTS

| | | |
|---|---|---|
| 6,692,451 B2 | 2/2004 | Splane, Jr. |
| 6,708,693 B1 | 3/2004 | Choy et al. |

(Continued)

*Primary Examiner* — Long V Le
*Assistant Examiner* — Bradley Impink
(74) *Attorney, Agent, or Firm* — Law Office of Leo Zucker

(57) ABSTRACT

A procedure and system for determining and placing spinal implants or prostheses includes measuring a change in position of vertebrae at an affected level of a patient's spine from a first position where the patient reports greatest pain at the affected level, to a second position where the patient reports least pain at the affected level. Spinal implants or prostheses are selected so as to urge the affected level of the spine toward the second position and away from the first position when the implants are placed at the affected level. In one embodiment, an implant device is formed by one or more inflatable balloons that are placed at determined locations inside a disc space at the affected level. When the balloons are inflated, vertebrae above and below the balloons are urged toward the second position and away from the first position at the affected level.

11 Claims, 36 Drawing Sheets

(51) Int. Cl.
   *A61B 19/00*   (2006.01)
   *A61B 17/02*   (2006.01)
   *A61F 2/44*    (2006.01)
   *A61F 2/30*    (2006.01)

(56) References Cited

U.S. PATENT DOCUMENTS

| | | |
|---|---|---|
| 6,860,272 B2 | 3/2005 | Carter et al. |
| 7,231,073 B2 | 6/2007 | Tanaka |
| 7,542,791 B2 | 6/2009 | Mire et al. |
| 2004/0171924 A1 | 9/2004 | Mire et al. |
| 2005/0054917 A1 | 3/2005 | Kitson |
| 2005/0165293 A1 | 7/2005 | Carter et al. |
| 2005/0177239 A1 | 8/2005 | Steinberg |
| 2006/0015030 A1 | 1/2006 | Poulin et al. |
| 2008/0108993 A1 | 5/2008 | Bennett et al. |
| 2009/0024164 A1 | 1/2009 | Neubardt |
| 2009/0299373 A1 | 12/2009 | Sisken |
| 2011/0092859 A1 | 4/2011 | Neubardt |
| 2012/0059419 A1 | 3/2012 | Alamin et al. |

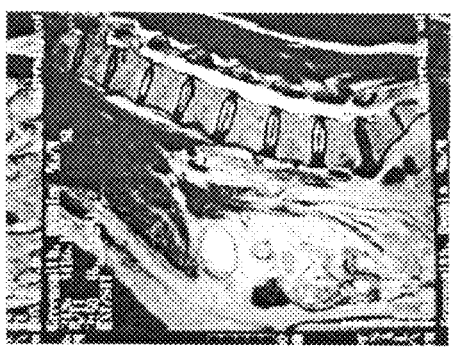
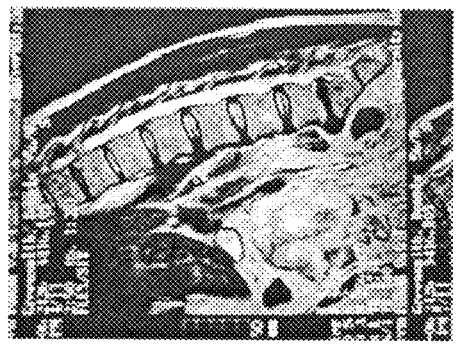
FIG. 16

L5S1 POSITION CHANGES FROM POP TO POC WILL BE MATCHED TO AN IMPLANT THAT CAN CREATE THOSE CHANGES IN THE SPINE AT LEVEL L5S1

- FLEXION: 9 DEGREES
- LATERAL BENDING: 5 DEGREES TO LEFT
- ROTATION: NEUTRAL
- COMPRESSION: ANTERIOR 2MM
- DISTRACTION: POSTERIOR 3MM

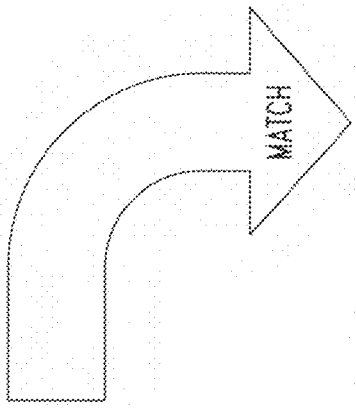

MATCH

PATIENT #1 WILL HAVE BEST CLINICAL RESULT WITH AN IMPLANT THAT PRODUCES A FLEXION/DISTRACTION FORCE ON THE L5S1 WHILE MAINTAINING NEUTRAL ROTATION. SUCH A DEVICE IS THE X-STOP IMPLANT.

FIG. 17

- EXTENSION: 6 DEGREES
- POSTERIOR TRANSLATION: 7MM L4 ON L5
- COMPRESSION: POSTERIOR 3MM
- DISTRACTION: ANTERIOR 1MM

L4/L5/S1 POSITION CHANGES FROM POP TO POC WILL BE MATCHED TO AN IMPLANT THAT CAN CREATE THOSE CHANGES IN THE SPINE AT LEVEL L4/L5/S1

- FLEXION, EXTENSION, LATERAL BENDING, ROTATION, TRANSLATION, COMPRESSION AND DISTRACTION CHANGES QUANTIFIED.

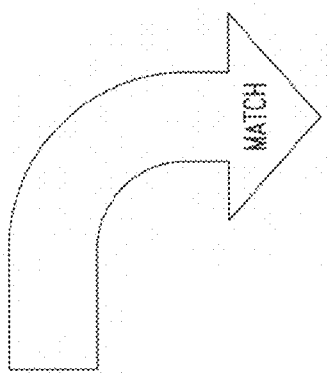

MATCH

PATIENT #2 WILL HAVE BEST CLINICAL RESULT WITH AN IMPLANT THAT PRODUCES A POSTERIOR COMPRESSION AND TRANSLATION OF L4 ON L5 WITH AN ANTERIOR DISTRACTION AND ANTERIOR TRANSLATION OF L5 ON S1. SUCH A DEVICE MAY BE A CUSTOM FABRICATED TWO LEVEL ARTIFICIAL DISC PROSTHESIS WITH POSTERIOR PEDICLE SCREW MOTION PRESERVATION STABILIZATION.

FIG. 25

BALLOONS MAY BE INTRODUCED INTO DISC SPACE PERCUTANEOUSLY

INTRODUCING BALLOONS INTO THE DISC SPACE

LATERAL BALLOON INFLATED TO CREATE LATERAL BENDING

POSTERIOR BALLOON INFLATION CREATES FORWARD FLEXION
BALLOON INFLATED UNTIL POC IS ACHIEVED

MULTIPLE BALLOONS APPLY FORCES TO VERTEBRAL BODIES
ABOVE AND BELOW

POSITIONS OF THE BODIES CHANGE IN THREE DIMENSIONS

DETERMINING AND PLACING SPINAL IMPLANTS OR PROSTHESES

CROSS REFERENCE TO RELATED APPLICATIONS

This application is a divisional of my U.S. patent application Ser. No. 12/898,871 filed Oct. 6, 2010, which is a continuation-in-part (CIP) of my application Ser. No. 12/215,097 filed Jun. 25, 2008, and now abandoned. The '097 application claimed priority under 35 U.S.C. §119(e) of my U.S. Provisional Patent Application No. 60/937,055 filed Jun. 25, 2007, titled "System for Treatment of Spinal Abnormalities Using Patient Selected Positions".

BACKGROUND OF THE INVENTION

1. Field of the Invention

The present invention concerns treatment of spinal abnormalities by the use of implants or prostheses, and a procedure and system for placing the implants or prostheses.

2. Discussion of the Known Art

Surgeons and clinical practitioners use radiographic tools such as MRI scans and X-rays along with their experience and intuition to evaluate if a patient's spine is within a so-called "normal" configuration. If not, the surgeon decides how much restoration or positional variance must be imparted to the spine in order to eliminate or reduce back pain using procedures such as, e.g., spinal fusion or disc replacement. Because any given surgeon's intuition is usually based on his or her training and the fellowship program he or she completed, the current practice of evaluating a patient's spine and identifying implant devices to treat suspected abnormalities is subject to uncertainties and often results in patient outcomes that vary widely.

Further, in addition to being concerned only with a "normal" range of spinal configurations, practitioners today are also concerned with identifying any static positions that may cause the patient to experience pain. For example, a patient may have a normal range of motion but still feel pain at one or more positions within range. Moreover, pain alone cannot be detected by way of a patient x-ray or scan.

U.S. Pat. No. 6,708,693 (Mar. 23, 2004) discloses a method and device for positioning a patient during MRI imaging diagnosis. The patient lies supine on a platform with their legs extended and feet in contact with a footrest, and a harness is worn above the area of the spine to be compressed and imaged. A pair of straps fixed to the harness pull the harness toward the footrest, thereby compressing and flexing the patient's spine as desired for imaging. U.S. Pat. No. 6,860,272 (Mar. 1, 2005) and U.S. Pat. Appl'n Pub. No. 2005/0165293 (Jul. 28, 2005) relate to a device having an adjustable footplate for immobilizing a patient and compressing the patient's skeleton, joints, and/or spine during imaging.

U.S. Pat. Appl'n Pub. No. 2005/0177239 (Aug. 11, 2005) discloses a method and apparatus for computerized spinal surgery with an implant device having an inflatable cavity for placement between end plates of adjacent vertebra. The publication also discloses a surgical procedure wherein the patient is mounted on a support table, a region of the patient's spine is imaged, a 3-D image file of the region is obtained and stored, and the file is used for planning and carrying out computer-controlled implant surgery. See pars. [0147-48] and [0995-98], and FIGS. 42 & 43 of the '239 publication.

As far as is known, however, no procedure or system has been proposed wherein an affected level of a patient's spine is scanned while the patient assumes a position of greatest pain or discomfort, and the same level is scanned again after the patient assumes a position of greatest comfort, and wherein the difference between the two positions is quantified to allow an implant device to be identified for maintaining the patient's comfort when the device is placed at the scanned level.

SUMMARY OF THE INVENTION

According to invention, a procedure and system for determining and placing spinal implants or prostheses includes measuring a spatial change in position of vertebrae at an affected level of a patient's spine from a first position at which the patient reports greatest pain, to a second position where the patient reports least pain, and selecting one or more spinal implants or prostheses that are configured to urge the affected level of the spine toward the second position and away from the first position when the implants are placed at the affected level.

According to another aspect of the invention, a procedure and system for determining and placing spinal implants or prostheses includes measuring a spatial change in position of vertebrae at an affected level of a patient's spine from a first position at which the patient reports greatest pain, to a second position where the patient reports least pain, and placing an implant device of one or more inflatable balloons at certain locations in a disc space of the affected level. When inflated, the balloons urge the adjacent vertebrae toward the second position and away from the first position at the affected level.

For a better understanding of the invention, reference is made to the following description taken in conjunction with the accompanying drawing and the appended claims.

BRIEF DESCRIPTION OF THE DRAWING FIGURES

In the drawing:

FIGS. 1(a) and 1(b) are frontal and lateral views of a patient's spine in a normal position;

Figures 10, 11, 12:
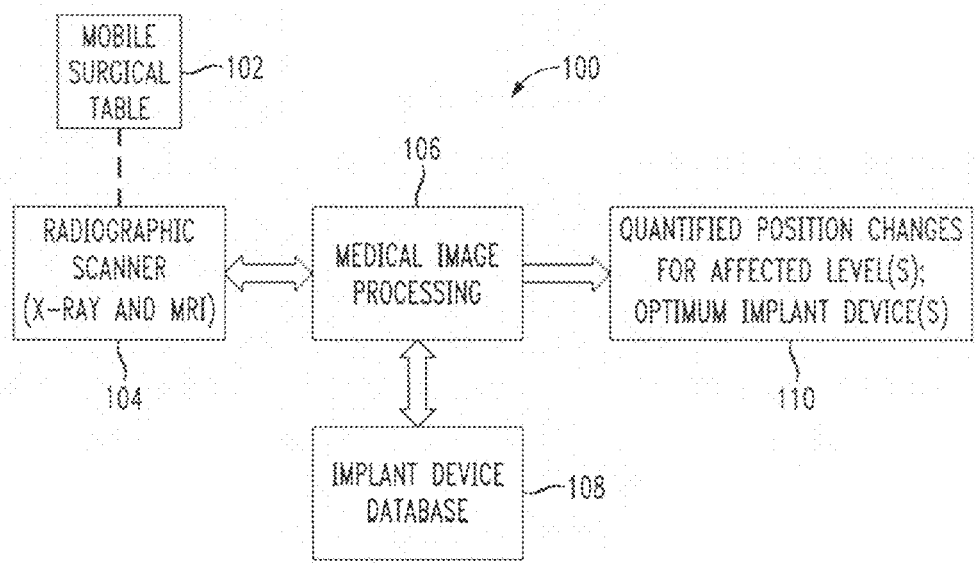

FIGS. 6 to 11 chart various steps to be taken when using a procedure for determining spinal implants according to the invention;

FIG. 12 is a block diagram of a procedure for determining spinal implants according to the invention;

FIGS. 13 to 25 illustrate two hypothetical case studies in which the inventive procedure may be applied;

FIGS. 26 to 35 are views of a first inflatable prosthesis device according to the invention; and FIGS. 36 to 39 are views of a second inflatable prosthesis device according to the invention.

DETAILED DESCRIPTION OF THE INVENTION

The present invention resides in a procedure and system for identifying an optimal spinal implant or prosthesis device for a given patient. Once a physician identifies a level of the patient's spine that is acting as a source of discomfort, an appropriate implant or prosthesis device is determined based on images of the relative configuration or positions of the vertebrae at the affected level taken at (i) a position of discomfort or pain (POP) whereat the patient reports experiencing the greatest amount of back pain, and (ii) a position of comfort (POC) at which the patient feels most comfortable. The relative positions of adjacent vertebrae at the affected level for the POP and the POC may be scanned using known tools, for example, fluoroscopy, x-ray, or CT scans, which tools are capable of yielding quantitative measurements of spinal distraction (elongation), compression (loading), flexion (bending forward), extension (bending backward), lateral bending, translation and rotation.

Images obtained at the POP and the POC for a group of patients have revealed that the POC for a given patient is usually a polar opposite from POP, and vice versa. For example, patients who are most comfortable with traction on their back, for example, by sitting in a chair flexed forward and leaning on their palms with arms fully extended, are usually most uncomfortable at positions that compress the back, such as standing. Given that a determined static position is capable of producing pain, then any motion that causes the patient's body to pass through the POP a multitude of times will be a most painful experience for the patient. That is, it is the repeated coincidence with the POP over the path of the motion that causes the pain, and not just the motion alone. Finding and maintaining the patient's POC at the affected level(s) and avoiding the POP should therefore be considered essential to a successful surgery.

Figure 1A:
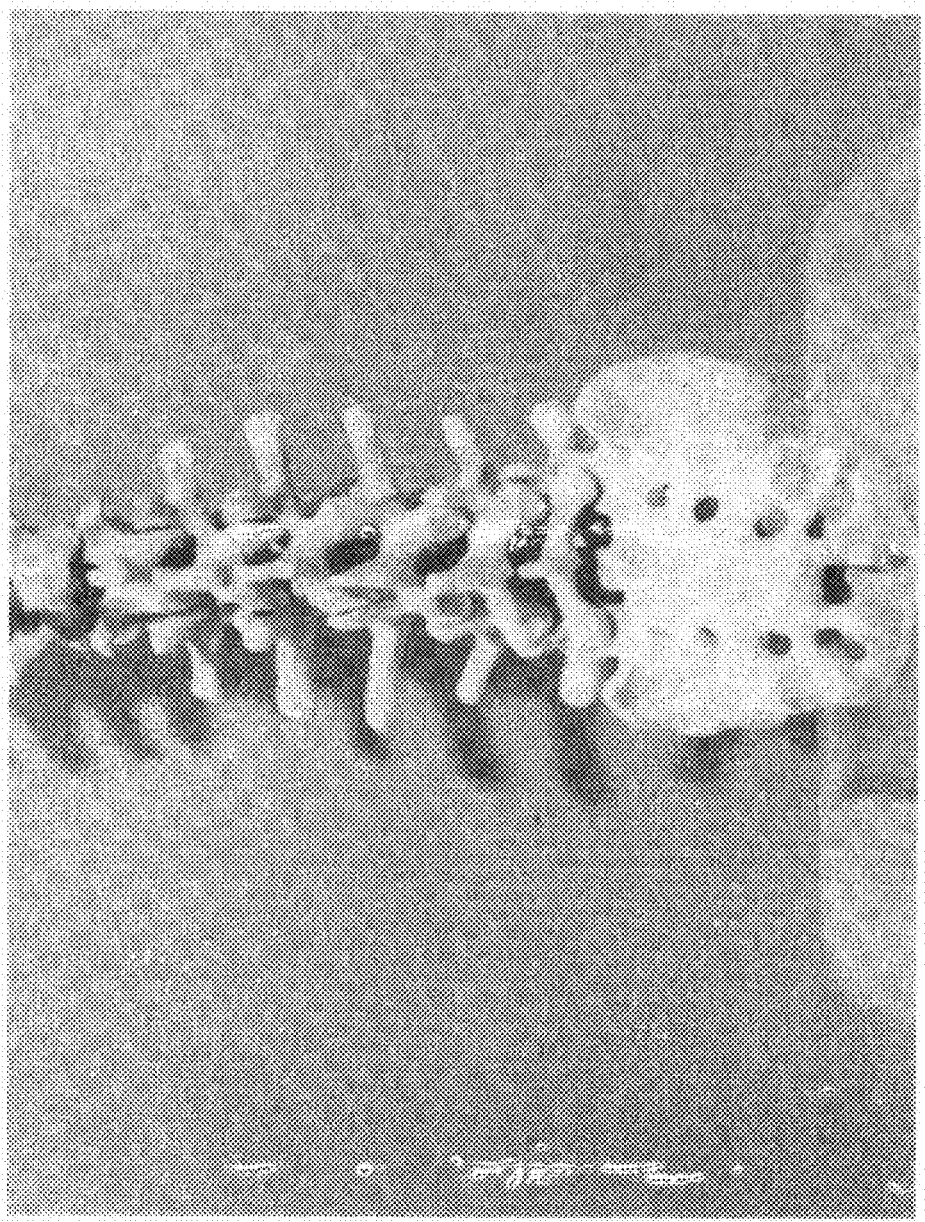
Figure 1B:
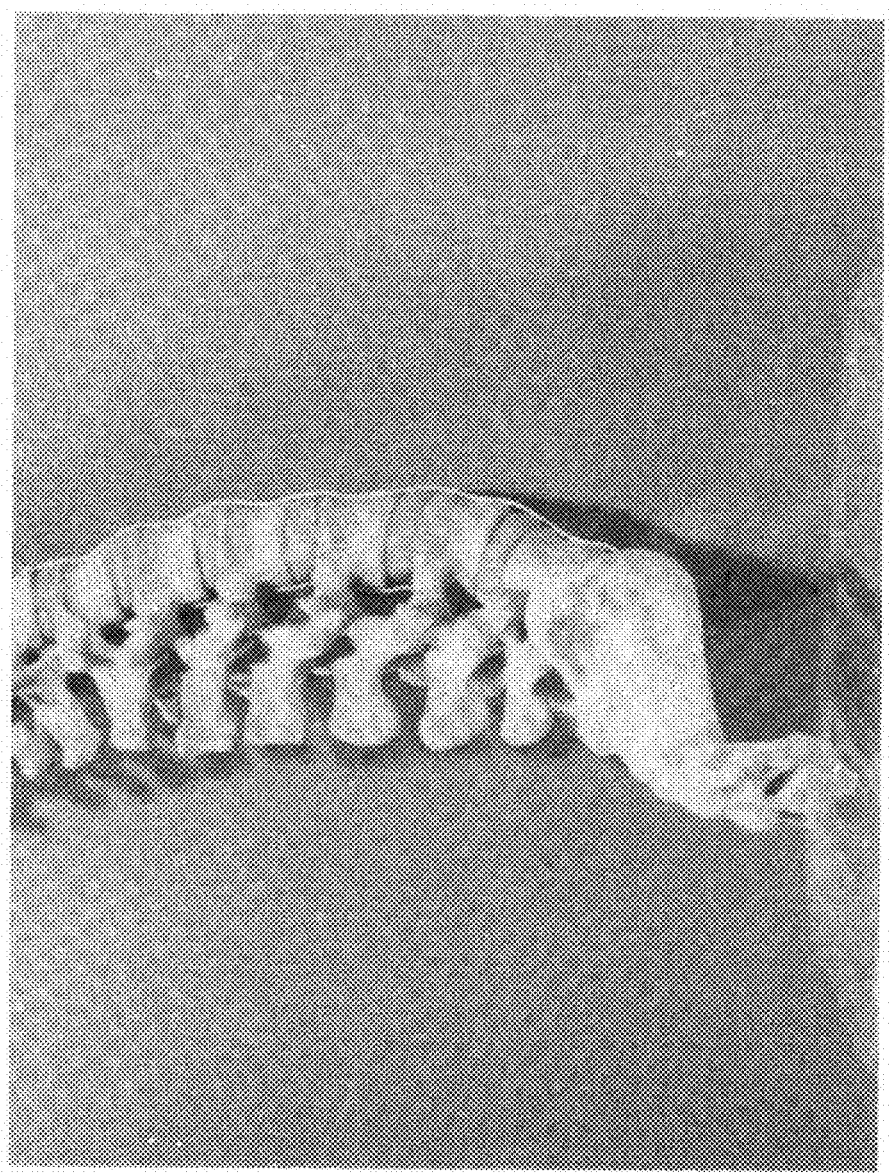
Figure 2:
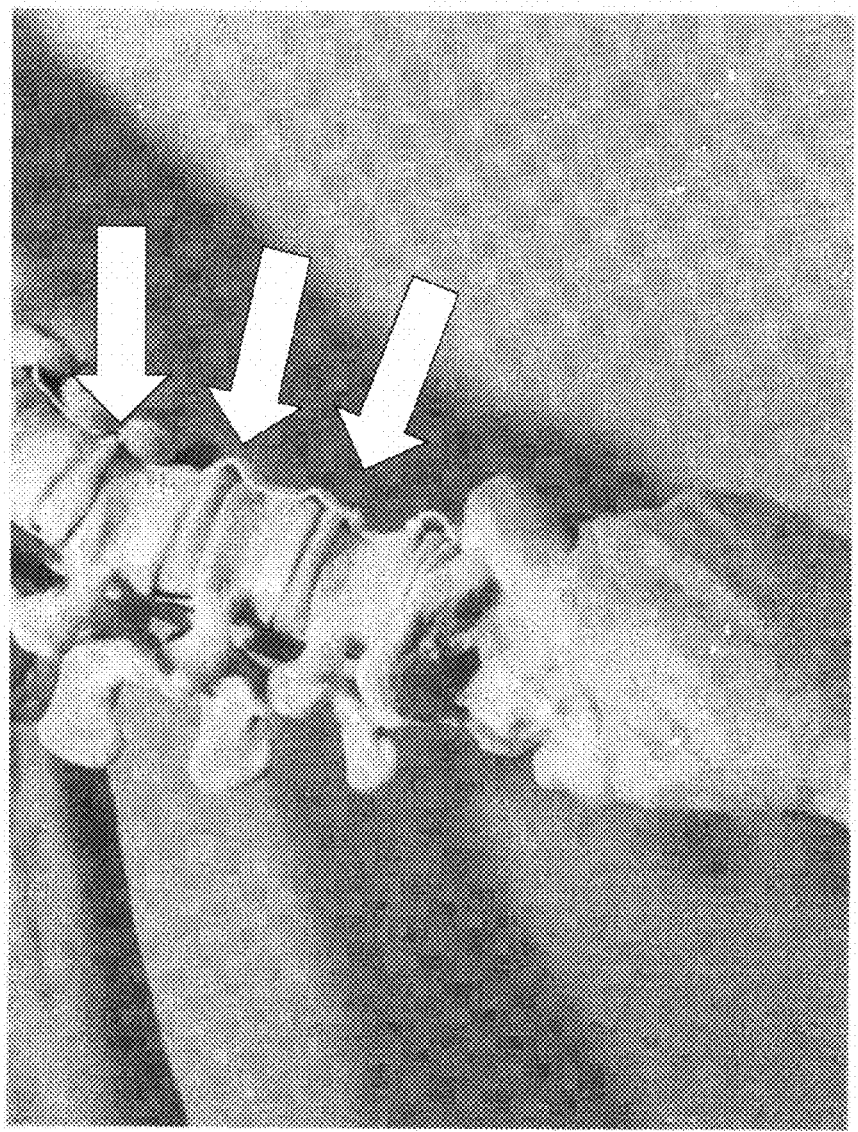
FIG. 2 is a view of the spine with full flexion applied.

Many patients can move their backs physically until they experience a POC for their spine. That is, patients may bend and contort using their spine as a lever arm about a painful level, and thereby effect a small change in the vertebral configuration at that level. FIGS. 1(*a*) and 1(*b*) are frontal (AP) and lateral views of a patient's spine when in a neutral or normal position. It will be appreciated that in order to effect a small change in the relative position of a single vertebra with respect to the immediately adjacent vertebrae, the spine as a whole must bend into an extreme position to act as a lever arm about the one vertebra. For example, FIG. 2 shows the position taken by the neutral spine in FIG. 1(*b*) with full flexion applied. This results in small changes in the positions of each level of the spine as indicated in FIG. 2, but at the same time creates an overall deformity of the spine.

According to the invention, one or more implant devices or prostheses are identified which when implanted at an affected level of a patient's spine, will urge vertebrae at the level into the position measured at the patient's POC, and inhibit the vertebrae from movement to the position measured at the patient's POP. For example, if the patient's POC is such that the configuration of the vertebrae at the affected level is one of flexion (rather than "normal"), then a device that creates flexion is implanted at that level. An example of such a device is the X-Stop® IPD® System. See step 42 in FIG. 11. And, if the patient's POP is such that the configuration of the vertebrae at the affected level is one of flexion, then a device that will prevent flexion (e.g., the Dynesys® Dynamic Stabilization System) is implanted. See step 44 in FIG. 11. Accordingly, the inventive procedure acknowledges that patients may experience back pain even though clinical examinations and scans of their spinal vertebrae may be normal, and the procedure identifies a patient's POP as a position to avoid within any spectrum of spinal motion that can otherwise be tolerated at the affected level.

As mentioned, patients with back pain frequently move their bodies into a position of comfort by contorting, bending, or distracting their torso in order to obtain their POC, and their position of maximal pain (the POP) often differs greatly from the POC. When studied radiographically (with x-rays or MRI), the two different positions may be compared, for example, by looking at the anatomic or spatial position of each vertebra in relation to the adjacent vertebrae. In the present procedure, the difference in anatomic position of the vertebral bones is documented by one or more known techniques such as x-ray or MRI, and then measured. A slight change in the relative position of the adjacent vertebrae at the affected level is recorded (e.g., digitally) and analyzed to create a motion model that illustrates the positions through which the spinal bones move from the POC to the POP. One example of a suitable radiographic imaging device is the "EOS 3-D" available from Biospace Med of Cambridge, Mass., U.S. A patient's POP and POC may also be measured or quantified by having the patient wear commercially available non-invasive electrogoniometers and/or torsiometers arranged to measure the range of motion of the patient's cervical and lumbar spine. The change of position from the POP to the POC is preferably measured and recorded in three planes.

Figure 3:
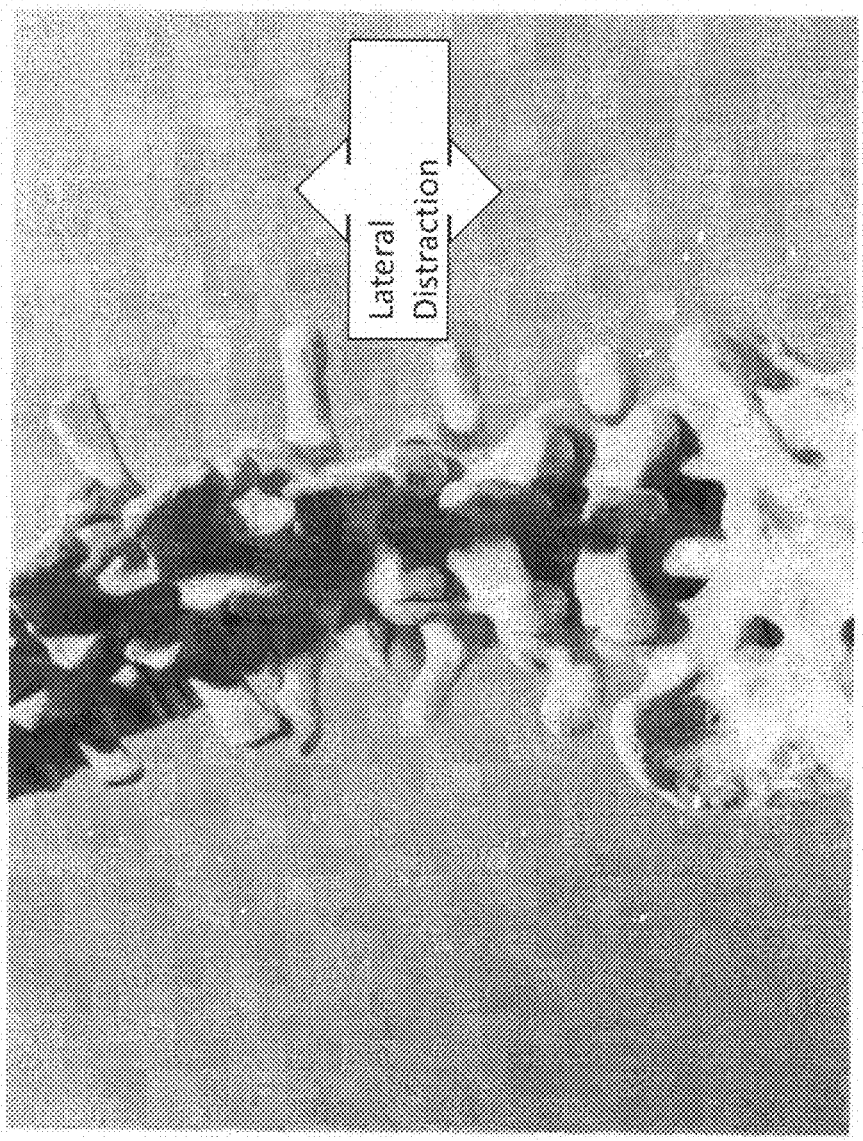
FIG. 3 is an AP/frontal view of the spine, showing forces required to achieve a position of comfort (POC) for the patient according to the invention.
Figure 4:
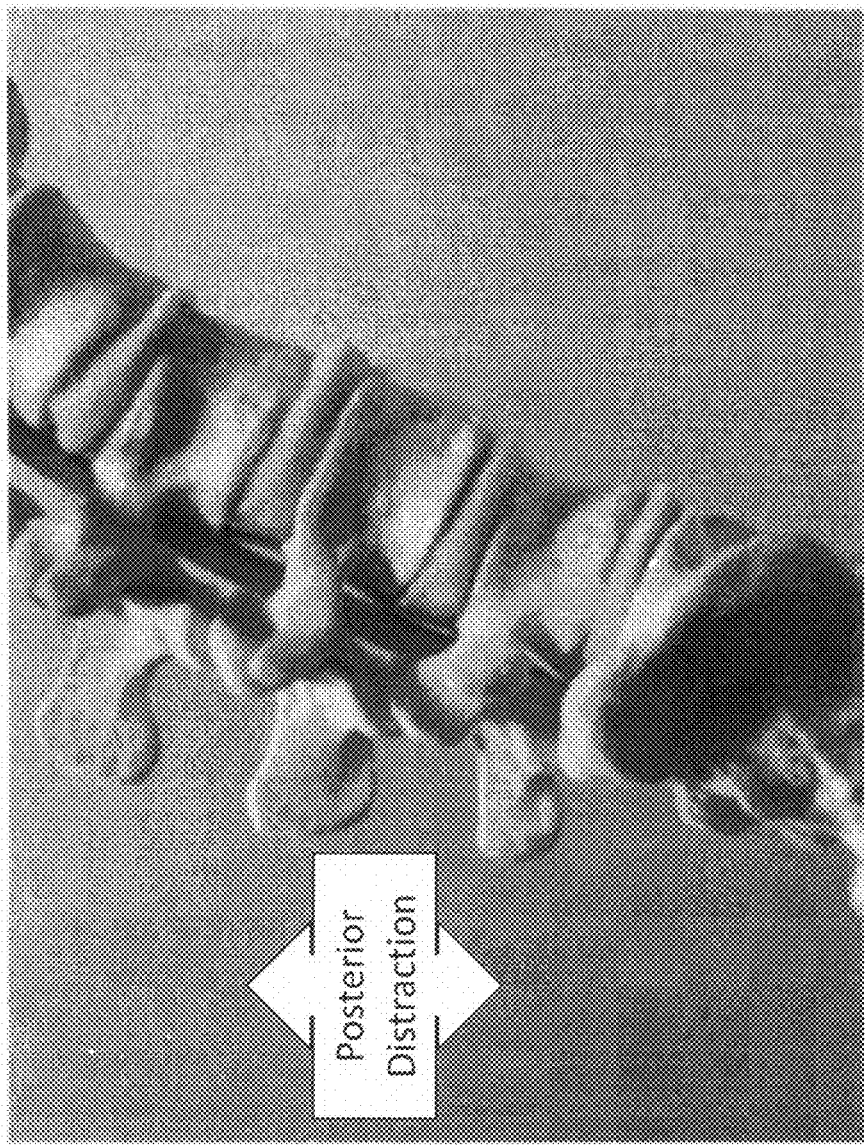
FIG. 4 is a lateral view of the spine, showing forces required to achieve the POC for the patient according to the invention.
Figure 5:
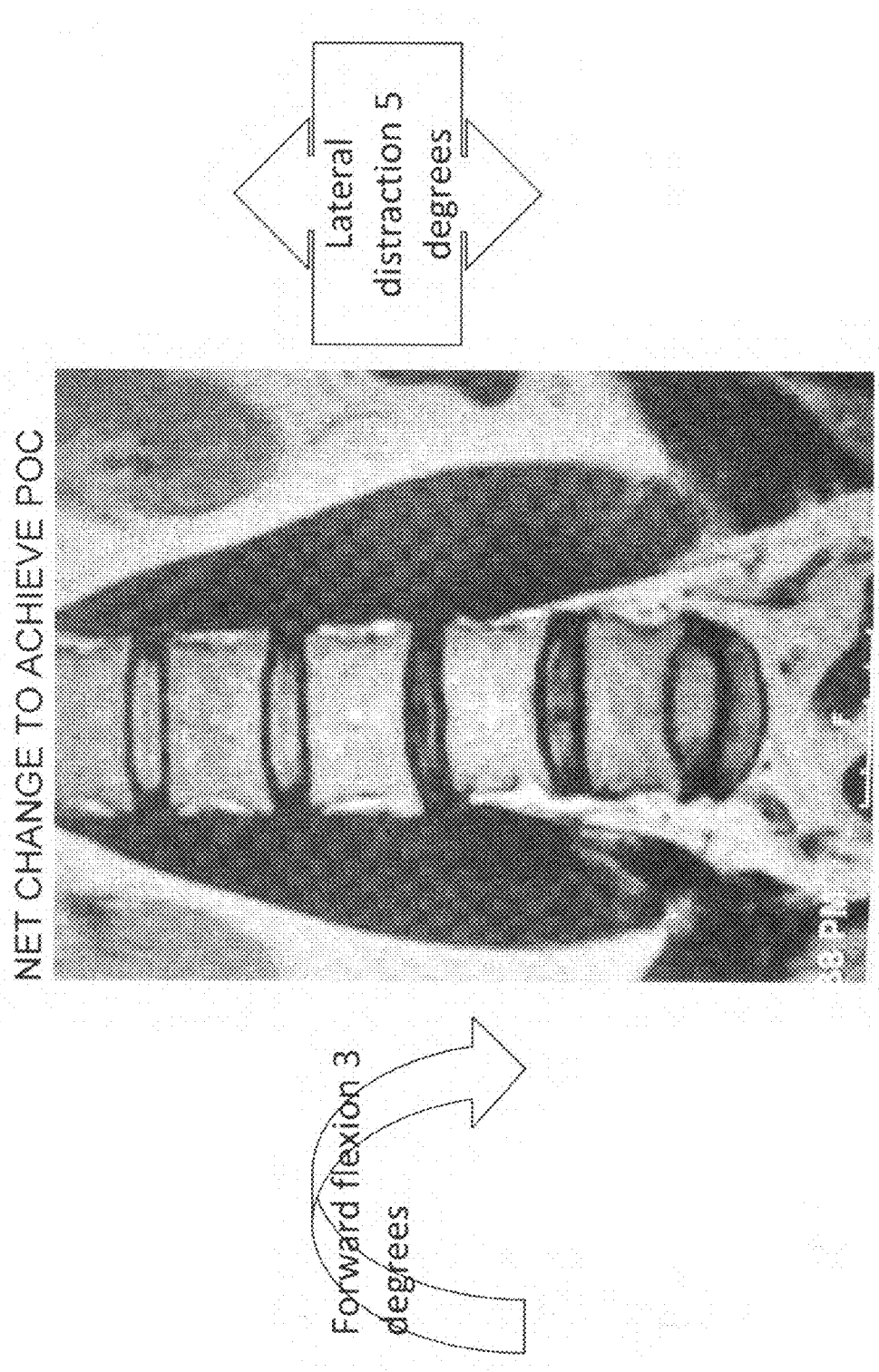
FIG. 5 is a view of the spine, illustrating a net change in position to achieve the POC according to the invention.
Figure 6:
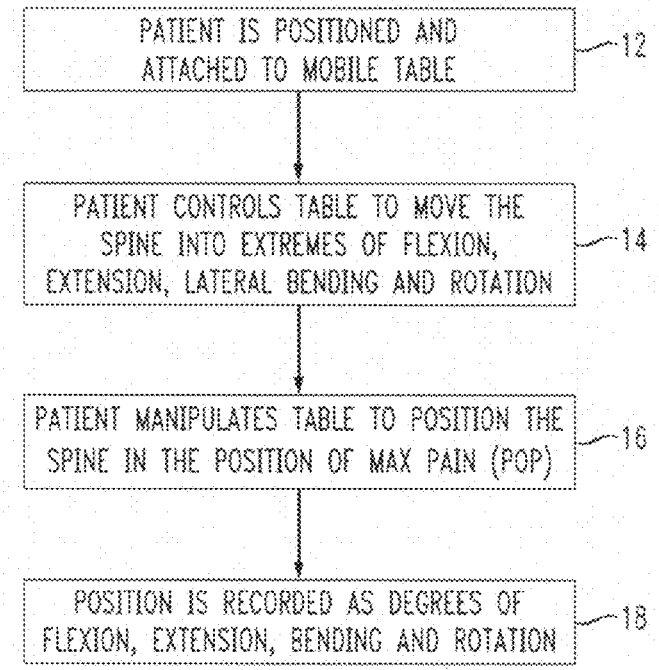
Figure 7:
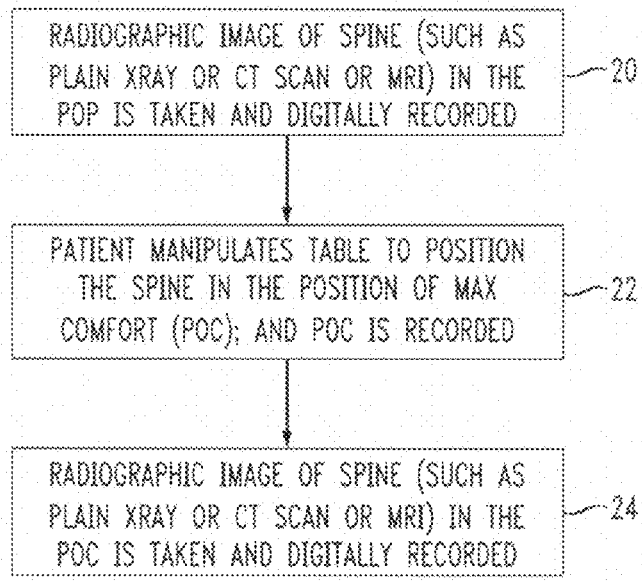
Figure 8:
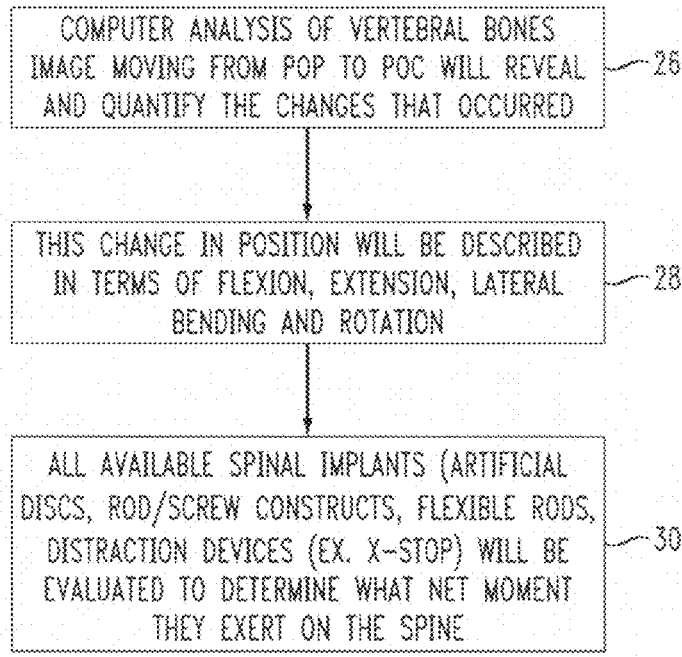
Figure 9:
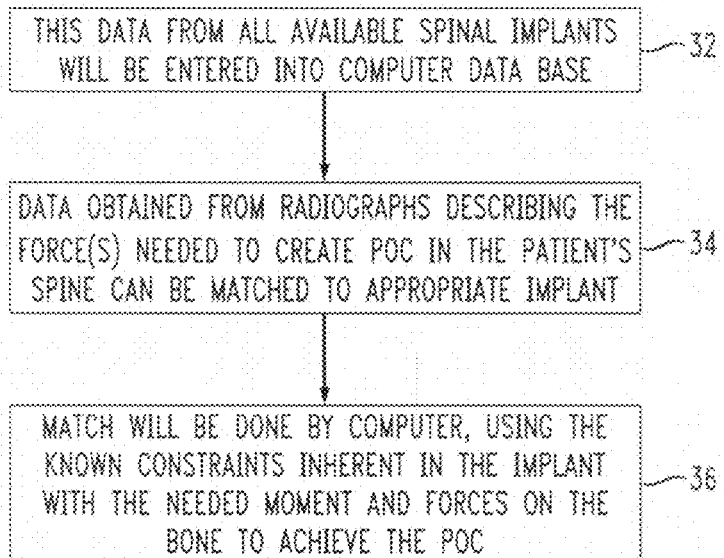

FIG. 3 is an AP/frontal view of a particular patient's lumbar spine, wherein the forces required to achieve a POC for the patient are illustrated as vectors in the drawing. FIG. 4 is a lateral view of the same region of the patient's spine, and also indicates the forces needed to achieve the POC for the patient. FIG. 5 illustrates the net change required at the affected level, namely, a forward flexion of three degrees, and a lateral distraction of five degrees.

Surgery is planned to transfer the patient's spinal bones into the configuration determined for the patient's POC according to the scans or physical measurements performed on the patient, and to maintain the bones in the determined configuration. This is accomplished, for example, either by fixing the bones in the desired configuration (e.g., a spinal fusion), or by using a device that allows motion but with such constraint as to avoid the configuration scanned for the patient's POP (e.g., by implanting an artificial disc replacement). For example, a patient that demonstrates maximal pain in flexion (bending forward) should receive a spinal implant that urges the vertebrae at the affected level toward spinal extension (bending backward). Given the current availability of spinal implants with various physical characteristics, it is likely that the surgeon will be able to select an appropriate implant in order to achieve the desired results.

As mentioned, different spinal implants allow for certain kinds of motion while constraining others. According to one aspect of the invention, data representing position and motion profiles for various spinal implants are entered into a database. See steps 30 and 32 in FIGS. 8 and 9, discussed below. A system processing unit (see FIG. 12 and related text, below) having access to the database then selects an optimal implant to achieve a desired alignment of the vertebrae at the affected level of a patient's spine, according to image data representing scans taken at the level for the patient's POP and POC.

In one scenario, a patient complaining of back pain is initially evaluated to determine if surgery is medically indicated. If so, the surgeon identifies the anatomic level(s) of the patient's spine that are the source of the pain using, e.g., a known discogram procedure that irritates each suspect level and monitors patient response. As illustrated by the charts of FIGS. 6 to 11, the patient is then secured on a table (step 12) constructed and arranged to move him or her into a number of different positions under the control of the patient (step 14). For example, a so-called SpineSix® table system available from MediCepts of Stuart, Fla. 34994. See U.S. Pat. No.

6,692,451 (Feb. 17, 2004). The table should be radiolucent or otherwise transparent to radiation that is present when scanning is performed.

The patient reports his or her position of maximal discomfort (POP) in step 16 and their position of maximal comfort (POC) in step 22. The two table positions are recorded (steps 18 and 22) and corresponding position data is saved in a system memory. Scans, e.g., CT scans, are taken of the affected level(s) for at least the patient's POP (step 20) and the patient's POC (step 24). The two scans may be visually compared with one another by the surgeon, and corresponding image data is entered into the system in steps 20 and 24.

In steps 26 and 28, the change in the configuration of the patient's spine needed at the affected level in order for the patient to be without pain is then determined in terms of such parameters as spinal distraction (elongation), compression (loading), flexion (bending forward), extension (bending backward), lateral bending, translation and rotation. Data corresponding to the change in the spine configuration may be produced by medical image processing apparatus such as disclosed in, e.g., U.S. Pat. No. 7,231,073 (Jun. 12, 2007) all relevant portions of which are incorporated by reference. Based on this data, one or more spinal implants that are maintained in the system database are matched with the affected level(s) of the patient's spine. See steps 34, 36 and 40 in FIGS. 9 and 10. As noted in step 38 in FIG. 10, the same data can be used to fabricate a custom implant that will provide the forces needed to urge the vertebrae at the affected level toward the desired configuration at the patient's POC. Once a match is found, a determination is made as to whether or not the implant would tend to allow the vertebrae at the affected level to assume the configuration scanned for the patient's POP. If so, the system searches for other potential implants until one having the required motion constraint is identified for the surgeon.

A significant advantage of the invention is an improved patient outcome that results from allowing the patient to report directly concerning his or her own POP and POC, while the surgeon is assured of and confirms the patient's own interpretation through objective measures such as radiography. That is, an important feature of the present procedure resides in that the pain threshold is allowed to be set by the patient, confirmed by the surgeon, and documented or recorded effectively using, e.g., radiographic means and/or a table position. The recorded information is then used intraoperatively as a gauge to compare and judge the ideal pain free state of the patient's spine.

A conventional surgical table may also be used to perform the POP/POC diagnostic test. The patient may position himself or herself preoperatively on the table immediately before surgery, once motion control apparatus associated with the table saves or "remembers" the patient's POC. Once the patient is under anesthesia, the apparatus may be configured or programmed to move the table into the position of comfort, thus guaranteeing that the spine will be fused or fixed in the position of comfort.

An intraoperative imaging scan may be taken to check the spinal position, and this information entered into the table control apparatus to move the table in such a way as to recreate the POC in the spine. Intraoperative tools for navigation (such as, e.g., the Medtronic "Stealth" system) use input information derived from preoperative imaging, intraoperative imaging, and reference points acquired by the surgeon from the surgical field. The position of comfort may also be entered into the navigation system preoperatively, and appear as an overlay on a computer monitor screen so that the surgeon can clearly see his/her goal to change the position of the spinal bones into the position of comfort. Once the POC has been achieved, the bones may be fixed or fused in that position. Likewise, if a motion implant such as an artificial disc is being implanted, then the surgeon can be sure the implant is holding the spine in the desired position of comfort.

FIG. 12 is a block diagram of one embodiment of a system 100 for determining spinal implants according to the inventive procedure, and FIGS. 13 to 25 illustrate two hypothetical case studies or examples wherein the system 100 may be applied to identify an implant that will obtain the best clinical result for each patient.

EXAMPLE ONE

Patient 1 is positioned and attached to a mobile surgical table 102 such as, e.g., the SpineSix table mentioned above. The patient controls the table 102 to move his/her spine into extremes of flexion, extension, bending, rotation, distraction and compression. The patient then manipulates the table to position their spine in a position where he or she experiences maximum pain (POP). The table position is recorded in terms of degrees of flexion, extension, bending, rotation, distraction and compression.

Figure 13:
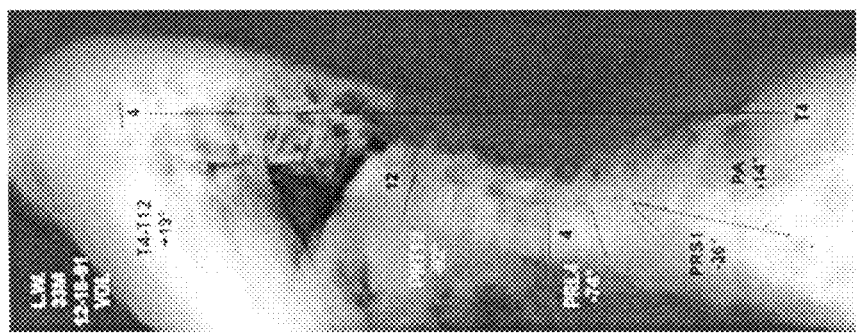

FIG. 13 is a radiographic image (plain x-ray) of the patient's spine in the POP, obtained from a scanner 104 in FIG. 12. The image, which may be taken and recorded digitally, is a plain lateral x-ray in which selected angles of lordosis and kyphosis associated with the motion segment are measured. In this example, MRI images are preferred instead of plain x-rays so that anatomical characteristics of the patient's POP and POC can be quantified once the positions are determined.

Figure 14:
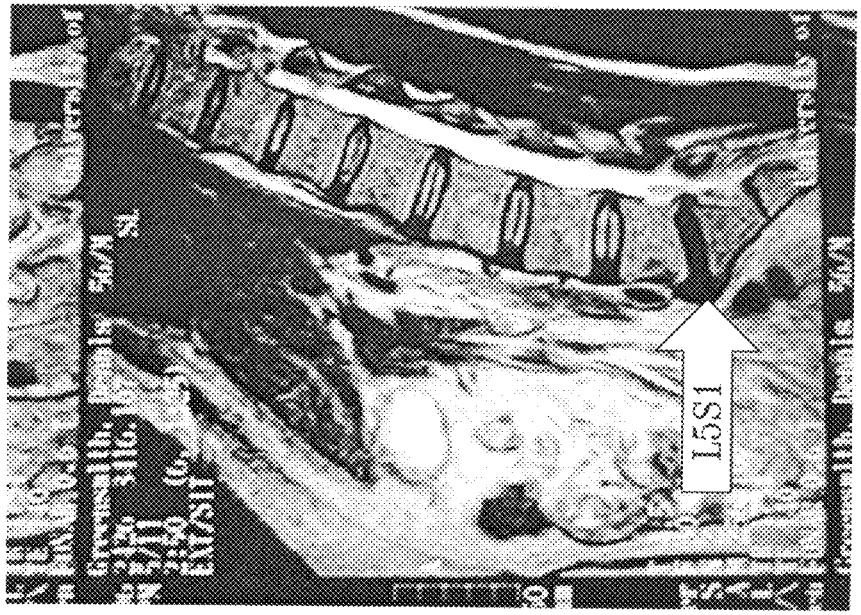

Radiographic MRI images of the patient's spine in the POP taken by scanner 104 are recorded, and FIG. 14 is the sagittal (lateral) view of the MRI taken with the patient in the POP. The lowest mobile segment (L5 S1) shows black disk on T2 weighted image (arrow), consistent with degeneration and is therefore the presumed spinal level of pain. Accordingly, the level with the arrow will be addressed with spinal surgery to keep the spine positioned in the POC as determined below, and not the POP.

Figure 15:
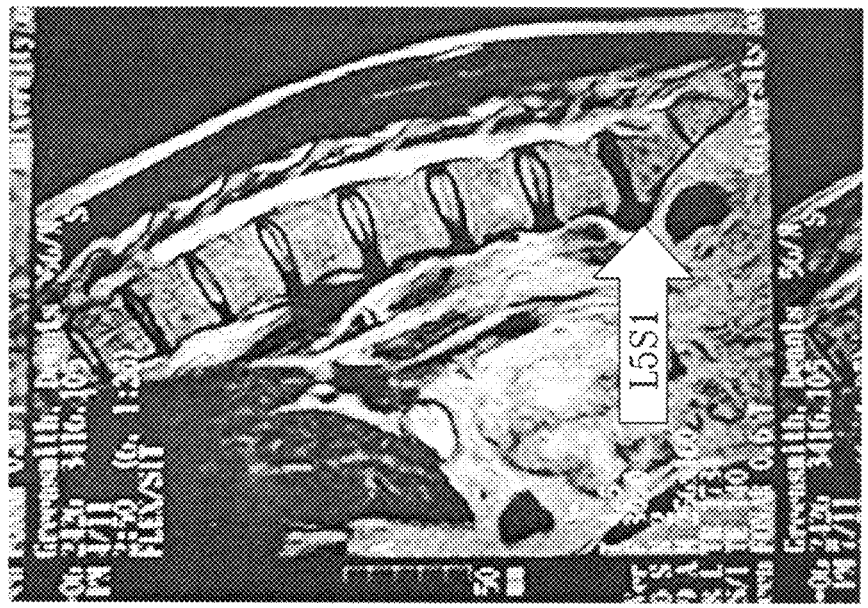

Patient 1 then manipulates the table 102 to place their spine in the position of maximum comfort (POC). The table position is again recorded as degrees of flexion, extension, bending, rotation, distraction, and compression. This position may be recalled during surgery. An MRI radiographic image of the spine in the POC is taken by scanner 104 and recorded, and FIG. 15 is the sagittal (lateral) view of the MRI taken with the patient in the POC. The lowest mobile segment (L5 S1) shows black disc consistent with degeneration (arrow) and is the presumed spinal level of pain.

The recorded image data is stored and processed using apparatus 106 such as disclosed in the mentioned '073 U.S. patent. The image data may be recorded and processed using established protocols. For example, measurements may be made using so-called OSIRIS software from the digital imaging unit at the University Hospital of Geneva, Switzerland. Further, a so-called DICOM (Digital Imaging and Communications in Medicine) protocol is a known standard for handling, storing, printing and transmitting information in medical imaging. DICOM includes a file format definition and a network communications protocol.

The recorded images of the vertebral bones at the patient's POP and POC reveal and quantify the change in the configuration of the bones in terms of flexion, extension, lateral bending, rotation, translation, compression and distraction. FIG. 16 illustrates the quantified changes in position (in degrees and millimeters) of L5 S1 from the POP to the POC. As shown in FIG. 17, the position changes are matched by the processing apparatus 106 to an implant that can create the changes in the spine at level L5 S1, wherein the implant is selected from among a number of implant devices (e.g., artificial discs, rod/screw constructs, flexible rods and distraction devices) whose characteristics are maintained in a system database 108. In this example, an output 110 of the processing apparatus 106 provides the quantified changes in position, and an indication that patient 1 should have the best clinical results with the above mentioned X-Stop implant which produces a flexion/distraction force on L5 S1 while maintaining neutral rotation.

EXAMPLE TWO

Patient 2 is positioned and attached to the mobile table 102. The patient controls the table 102 to move his/her spine into extremes of flexion, extension, bending, rotation, distraction, and compression. The patient then manipulates the table to a position where he or she experiences maximum pain (POP). The table position is recorded in terms of degrees of spinal flexion, extension, bending, rotation, distraction and compression.

Figure 18:
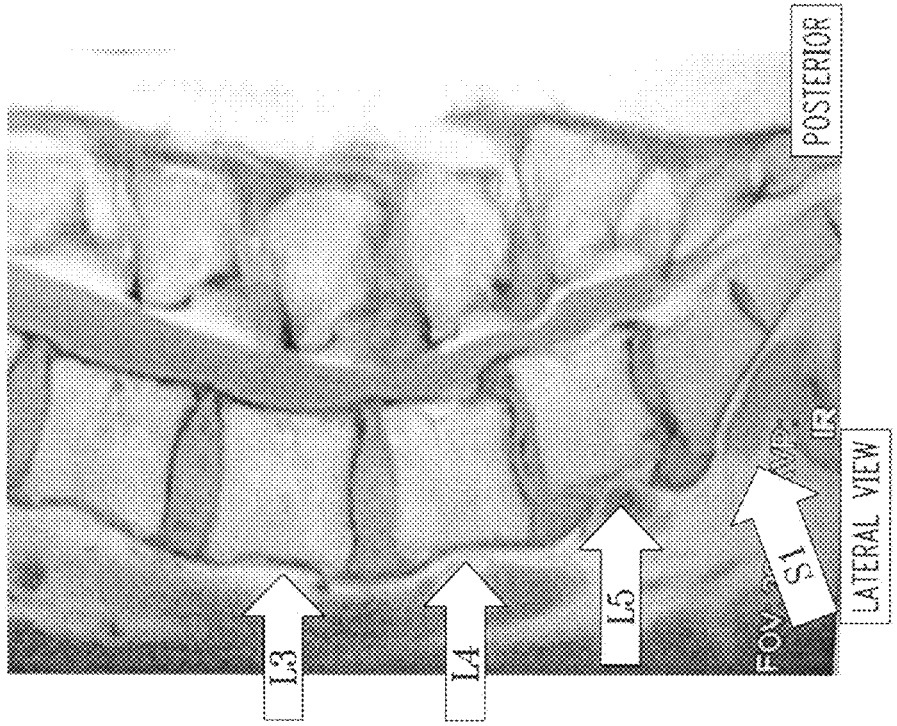

MRI radiographic lateral and coronal images of the patient's spine in the POP are taken separately by the scanner 104 and recorded. FIG. 18 shows the sagittal (lateral) view of the MRI taken with patient 2 in the POP. The image of FIG. 18 reveals anterior shift of L4 on L5 which is consistent with instability at that level and therefore presumed to be a spinal level of pain. Further, the image shows a posterior shift of L5 on S1 which is consistent with instability at that level and is therefore also presumed to be a spinal level of pain. Accordingly, the two levels with instability will be addressed with spinal surgery to keep the spine positioned in a POC, and not in the POP. The POC is determined as follows.

Figure 19:
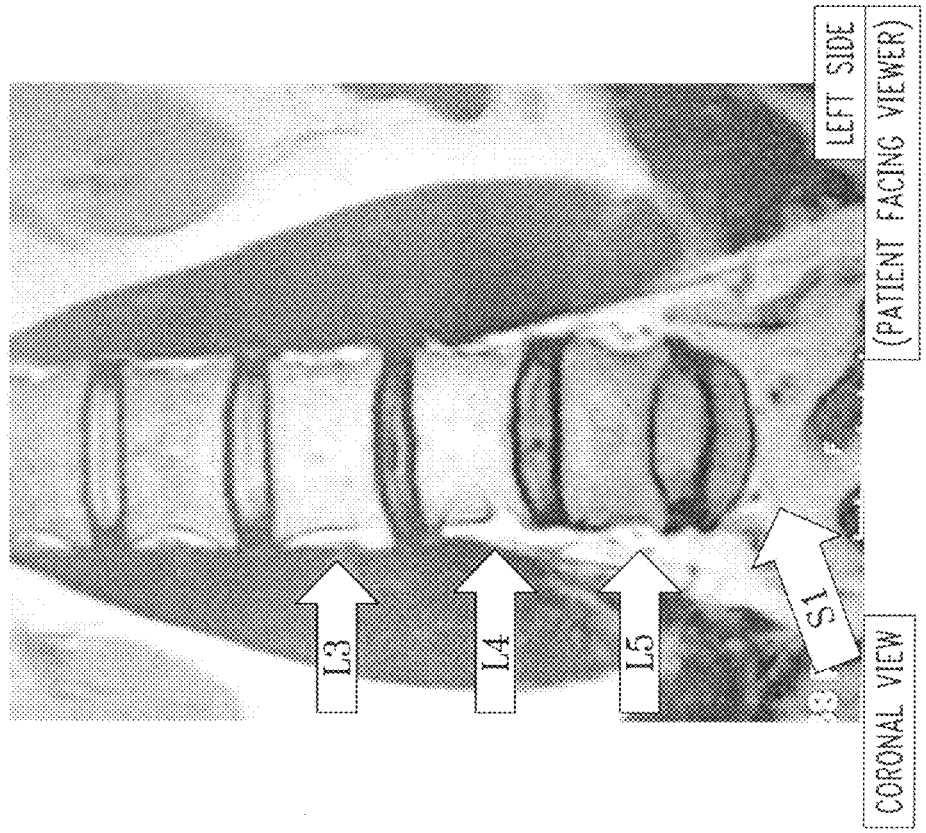

FIG. 19 is the coronal view of the MRI with patient 2 in the POP. The image reveals slight right lateral bending of L4 on L5. The patient then manipulates the table 102 to a position where their spine is at maximum comfort or POC. The table position is recorded as degrees of spinal flexion, extension, bending, rotation, distraction and compression. This position may be recalled during surgery.

Figure 20:
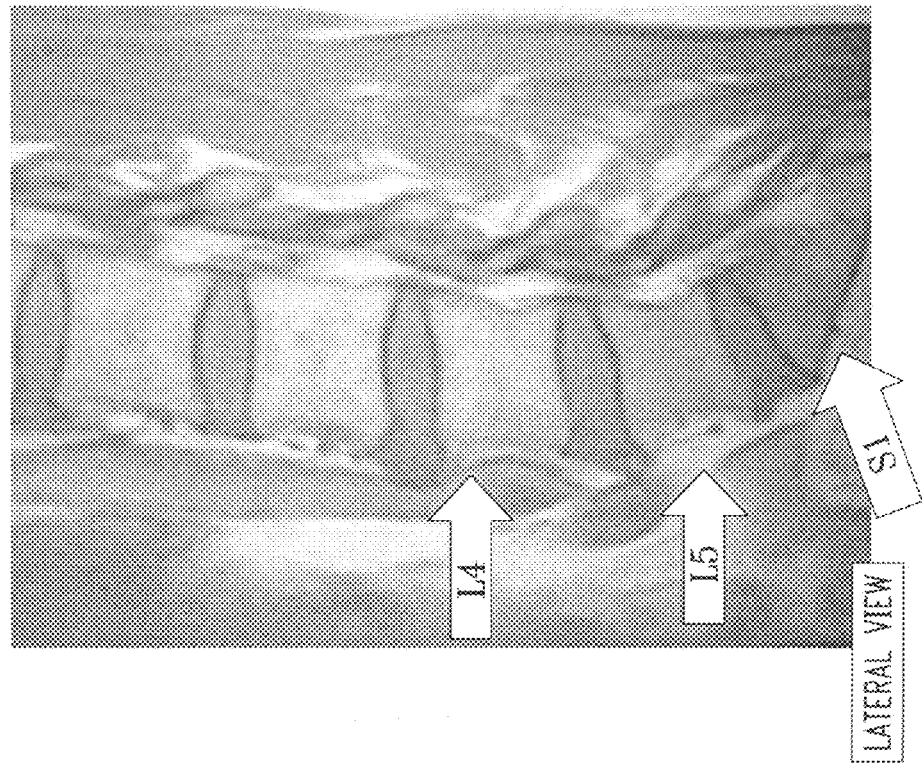
Figure 21:
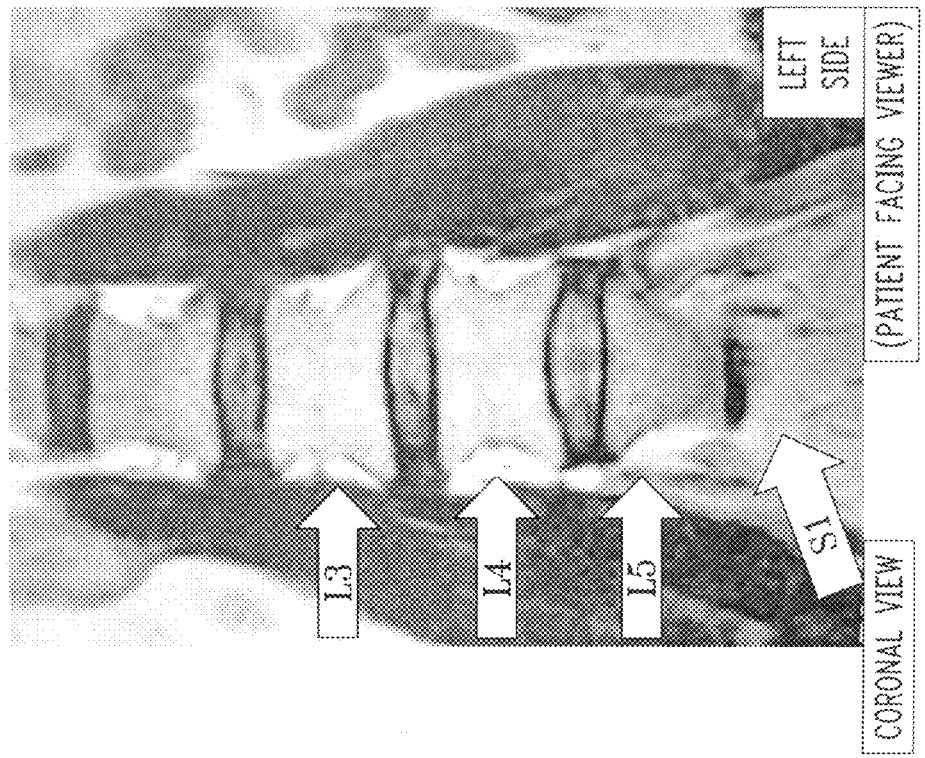

An MRI radiographic lateral image of the spine in the POC is then taken by the scanner 104 and recorded. The image in FIG. 20 is the sagittal (lateral) view of the MRI taken with the patient in the POC. MRI radiographic coronal images of the spine in the POC are also taken by scanner 104 and recorded. FIG. 21 is the coronal view of the MRI taken with the patient in the POC. The image reveals correction to neutral of lateral bending of L4 on L5.

The recorded image data is stored and processed by the image processing apparatus 106 as in EXAMPLE ONE. The recorded images of the vertebral bones at the patient's POP and the POC reveal and quantify the change in the configuration of the spinal bones in terms of flexion, extension, lateral bending, rotation, translation, compression and distraction.

Figure 22:
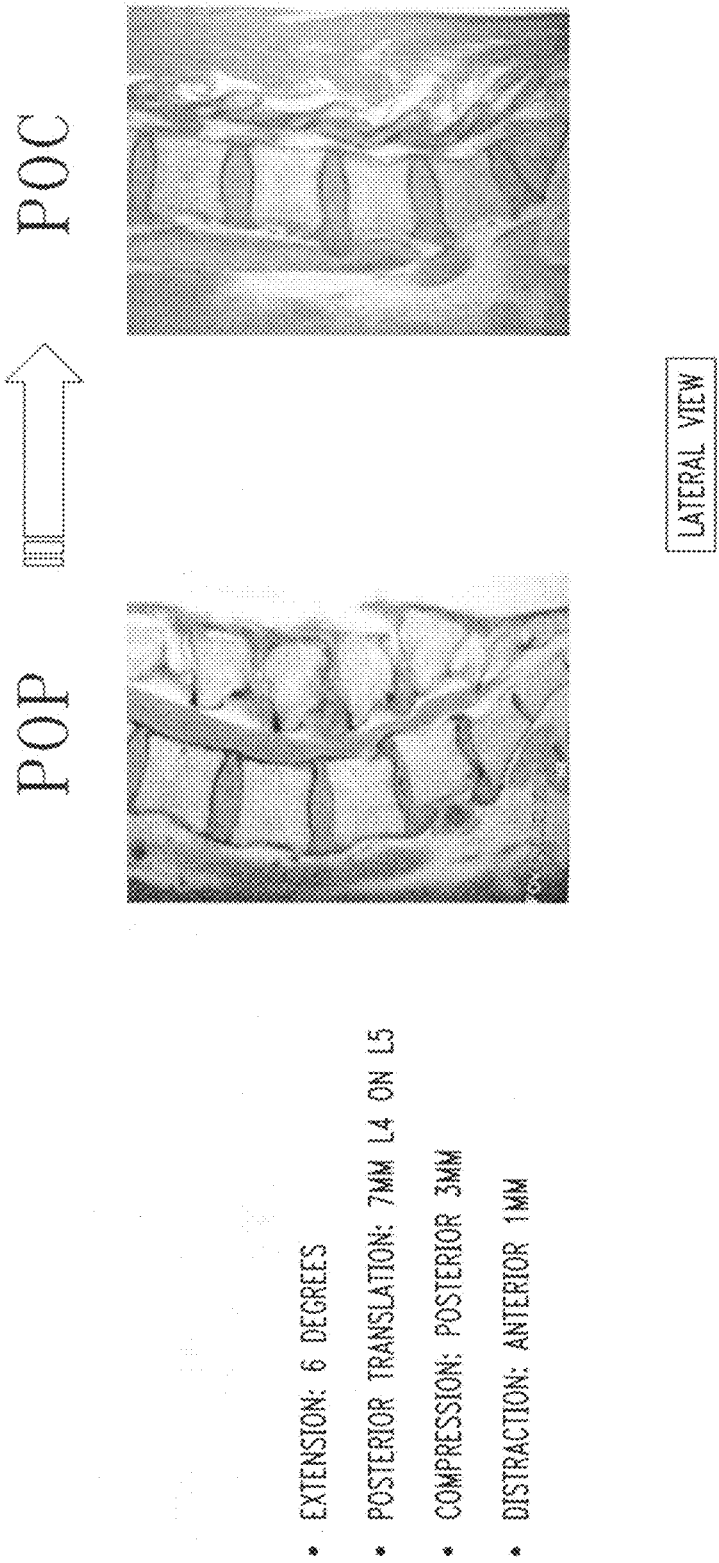
Figure 23:
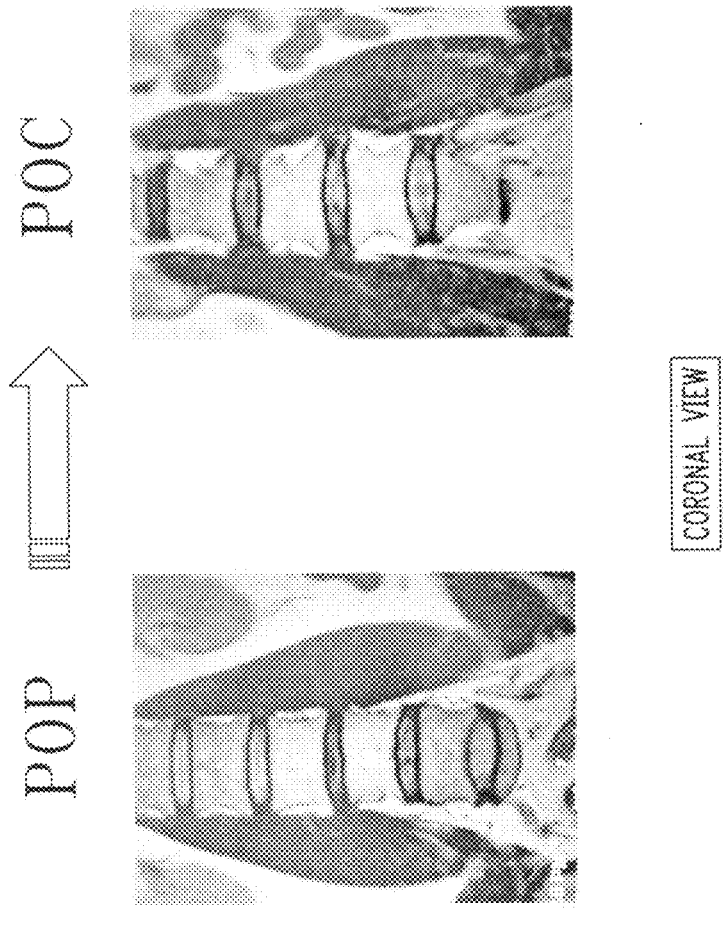
Figure 24:
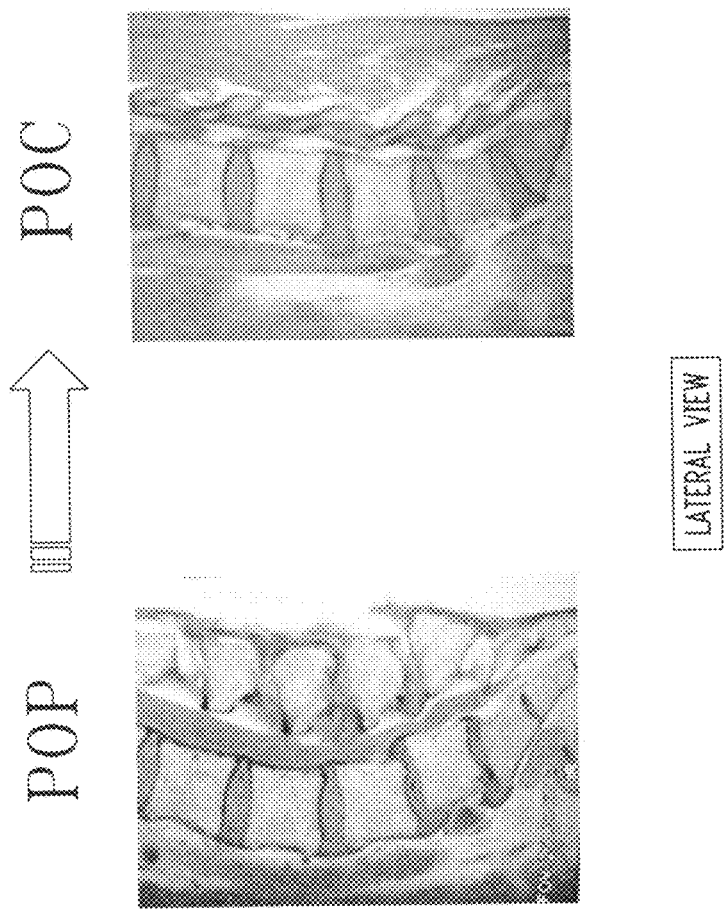
Figure 26:
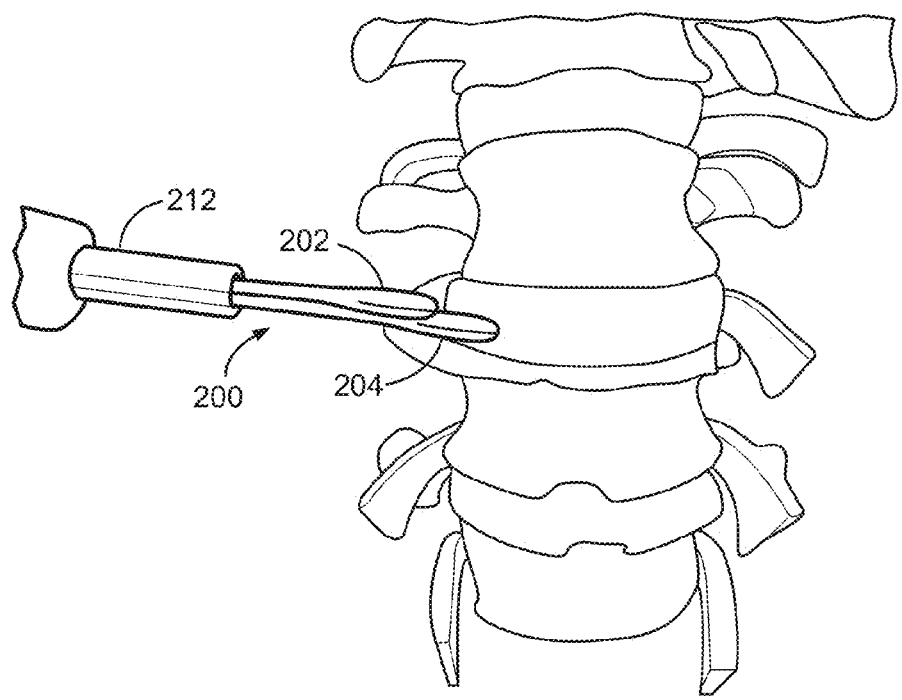

FIG. 22 illustrates the quantified changes in position (in degrees and millimeters) of L4-L5 from the POP to the POC in lateral view, and FIG. 23 shows the quantified changes in position of L4-L5 from the POP to the POC in coronal view. FIG. 24 illustrates the quantified changes in position of L5-S1 from the POP to the POC in lateral view.

As shown in FIG. 25, the position changes in L4/L5/S1 from the POP to the POC for patient 2 are matched by the processing apparatus 106 to an implant that can create the changes in the spine at levels L4/L5/S1. In this example, the output 110 of the apparatus 106 indicates that patient 2 should have the best clinical results with an implant that produces a posterior compression and translation of L4 on L5, with an anterior distraction and an anterior translation of L5 on S1. The implant may be selected from among a number of implant devices whose characteristics are maintained in the system database 108, or the device may be a custom fabricated two level artificial disc prosthesis with posterior pedicle screw motion preservation stabilization.

The implant device(s) required to achieve the correct POC for any patient may also be custom fabricated by way of balloons that are placed at determined locations between the adjacent vertebrae at each level to be treated, and then inflated to achieve the desired correction as explained further below.

Accordingly, to achieve a patient's POC, an appropriate implant or prosthesis device may be (i) provided as a custom implant preconfigured to impart the required force vectors, (ii) constructed in situ by "building" a framework within a disc space or externally to the patient's spinal vertebrae, and/or (iii) provided in the form of inflatable balloons constructed and arranged to expand within or outside a disc space to produce the required forces.

Custom Made Prosthesis to Achieve POC

Once CT scans and/or other imaging studies of a patient's spine at the POP and the POC produce the measurements that are needed to maintain the POC and to avoid the POP, a custom prosthesis may be fabricated prior to surgery such as, for example, a disc replacement device using CAD technology. Such replacement devices may be obtained, for example, from Ranier Technology Limited, Cambridge, UK, under the trademark Cadisc-L®. If necessary, the prosthesis can be sectioned and then assembled in the affected disc(s) at the time of surgery.

In Situ Constructed Prosthesis

A prosthesis may be constructed in situ by building a framework within an affected disc space or externally to the spine vertebrae, in order to achieve a patient's POC. For example, data corresponding to the patient's POC and the POP are obtained from preoperative imaging studies, and entered into an intraoperative navigation system (e.g., the mentioned Stealth system). A surgeon or a robotic mechanism then manipulates the patient's spinal segments into a configuration required to achieve the POC and to avoid the POP, according to information obtained from the navigation system based on the entered data. Once the POC is achieved, the surgeon can use established spinal instrumentation (e.g., screws, rods, cages, and/or plates) to maintain the vertebral configuration required for the POC.

In Situ Constructed Prosthesis with Intraoperative Visual Overlay

Using the data obtained from the preoperative imaging studies, the intraoperative navigation system may be configured in a known manner to produce image guidance overlays of the spine when at the POP and the POC, relative to the configuration of the spine in real time. The surgeon (or a robotic mechanism) then manipulates the spinal vertebral bones (e.g., by adjusting pedicle screws) until the navigation system confirms when the POC has been achieved. Spinal implants are then used to maintain the POC. For example, if the POC is achieved when the patient bends toward the left, implants placed on the right side of the spine will create distraction and produce the same forces as when the patient is bending to the left.

Inflatable Prosthesis

An implant or prosthesis may be constructed to be inflatable, and dimensioned to expand within or outside of a disc space in order to produce forces required to achieve a patient's POC. Such a prosthesis may be inserted percutaneously via a known insertion tool or cannula, or placed in the disc space by way of open surgery. For example, a prosthesis device 200 using two balloons 202, 204, is shown in FIGS. 26 to 35. One balloon 202 may be placed laterally on the (patient's) right side of a disc space 210, and then inflated to create a lateral distraction of, e.g., five degrees, thereby bending the spine to a patient's left and toward the configuration required for the patient's POC. The other balloon 204 may then be placed posterior in the disc space 210, and then inflated to create flexion of, e.g., three degrees so as to bend the spine forward and into the required configuration for the patient's POC.

Inflatable balloons the same or similar to those used in the known Kyphon® balloon kyphoplasty, wherein balloons are inserted through cannulas into fractured vertebral bones and then inflated to facilitate bone repair, may also be used in the prosthesis device 200. See, e.g., U.S. Pat. Appl'n Pub. No. 2009/0299373 (Dec. 3, 2009), all relevant portions of which are incorporated by reference. The device 200 includes an associated insertion tool 212 that is constructed and arranged in a known manner to introduce the balloons 202, 204 into the disc space 210 percutaneously, and to inflate the balloons as illustrated in the drawing.

Figure 27:
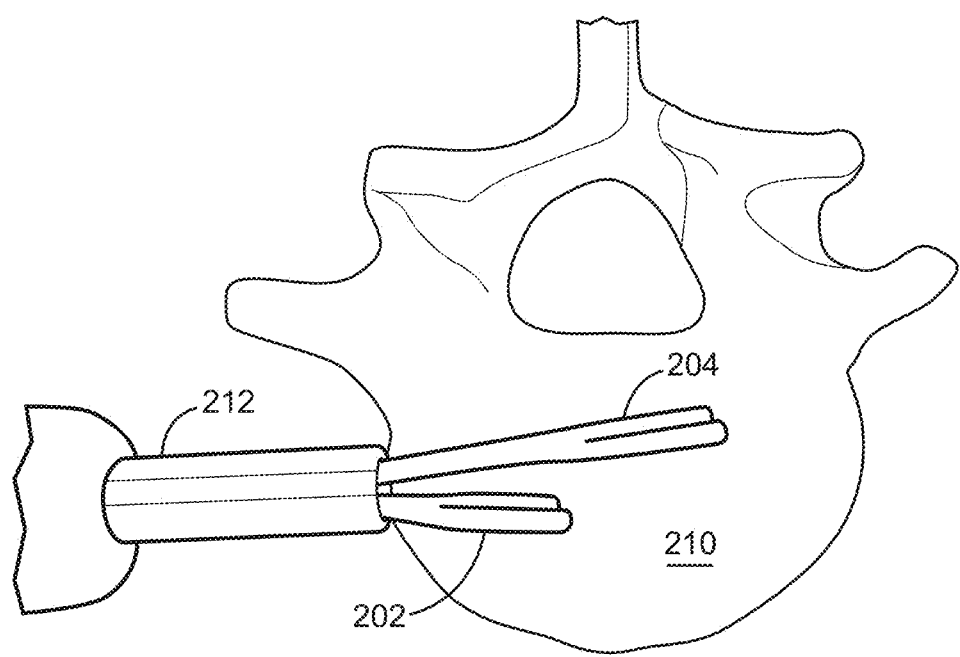
Figure 28:
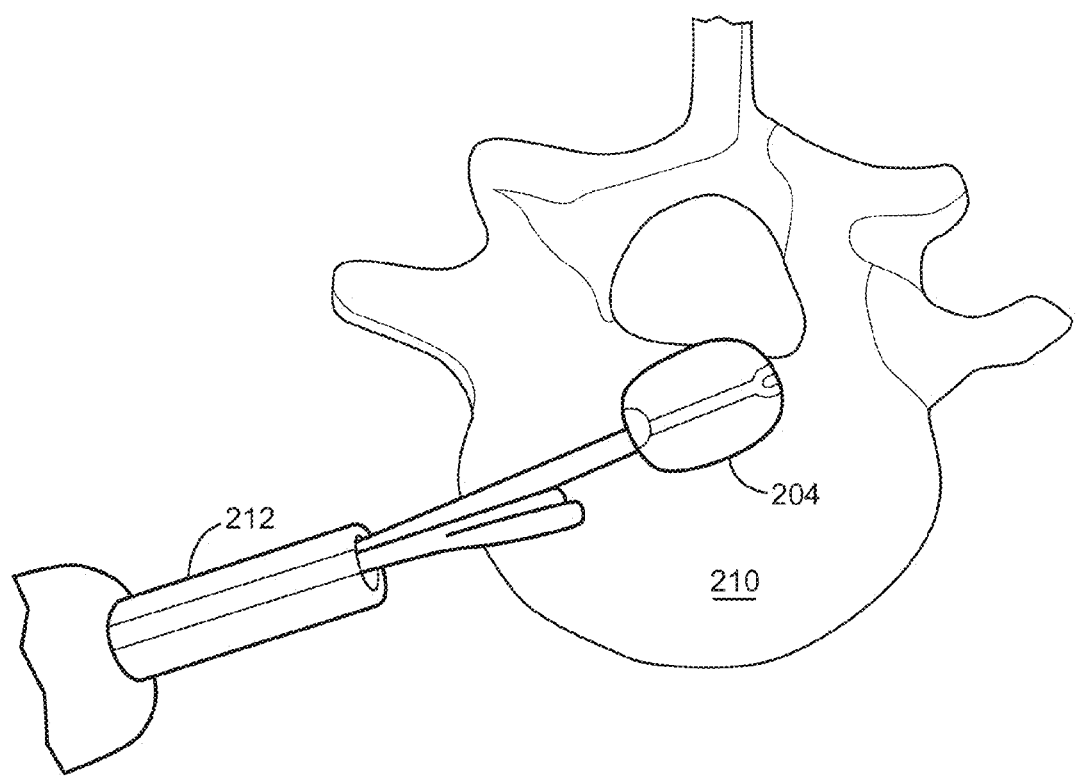
Figure 29:
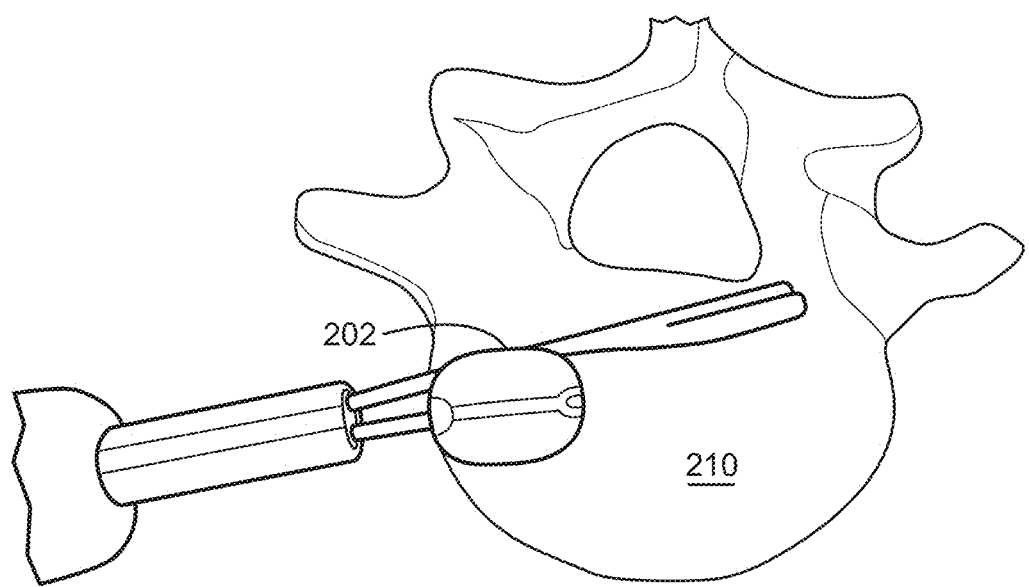
Figure 30:
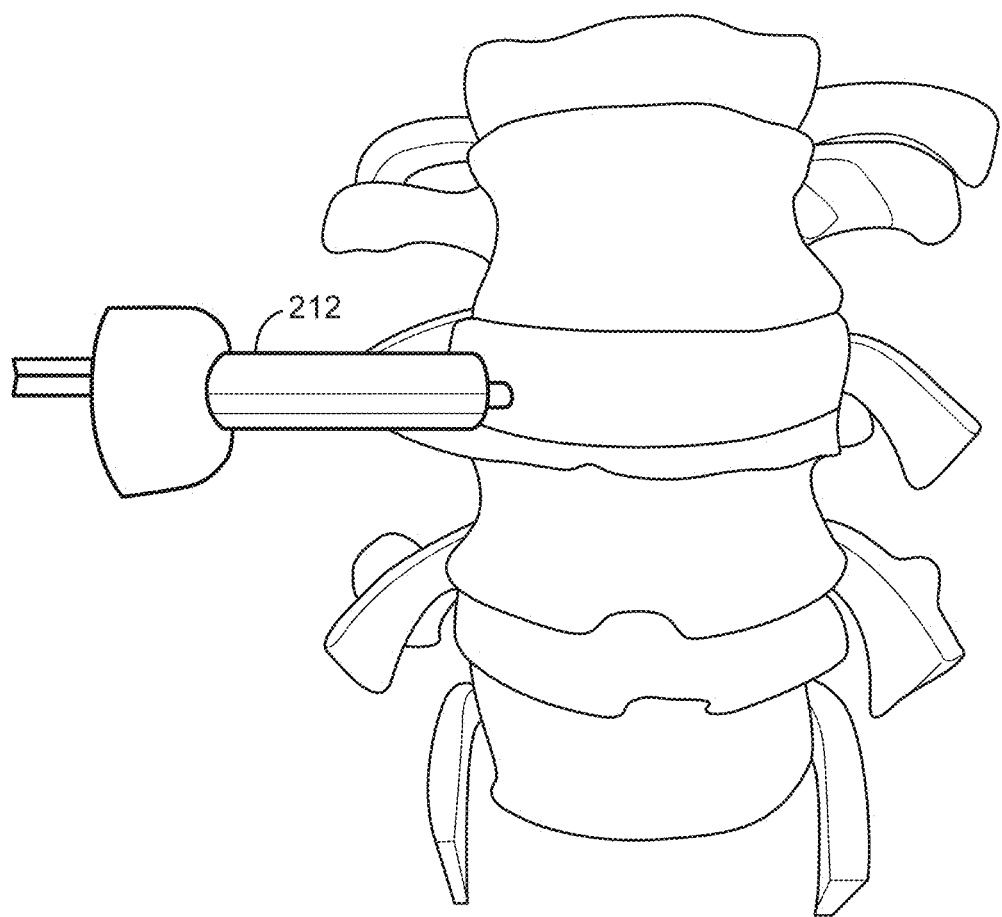
Figure 31:
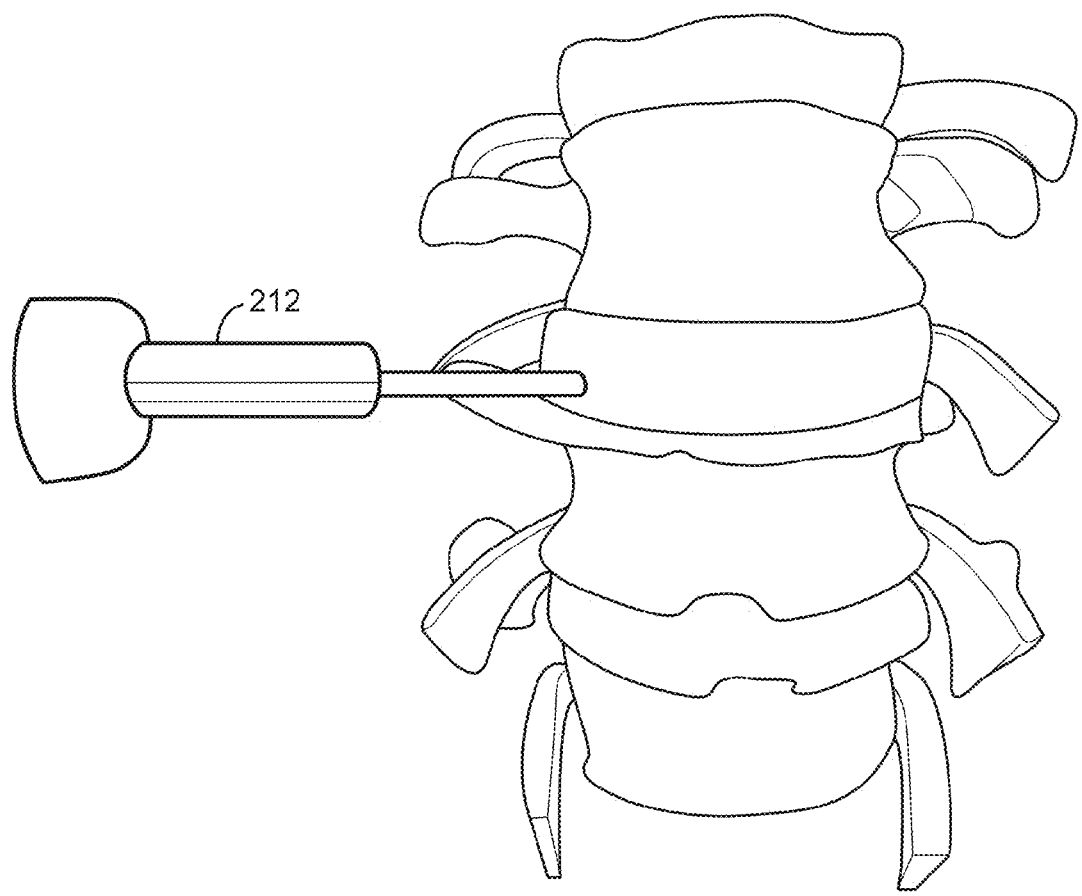
Figure 32:
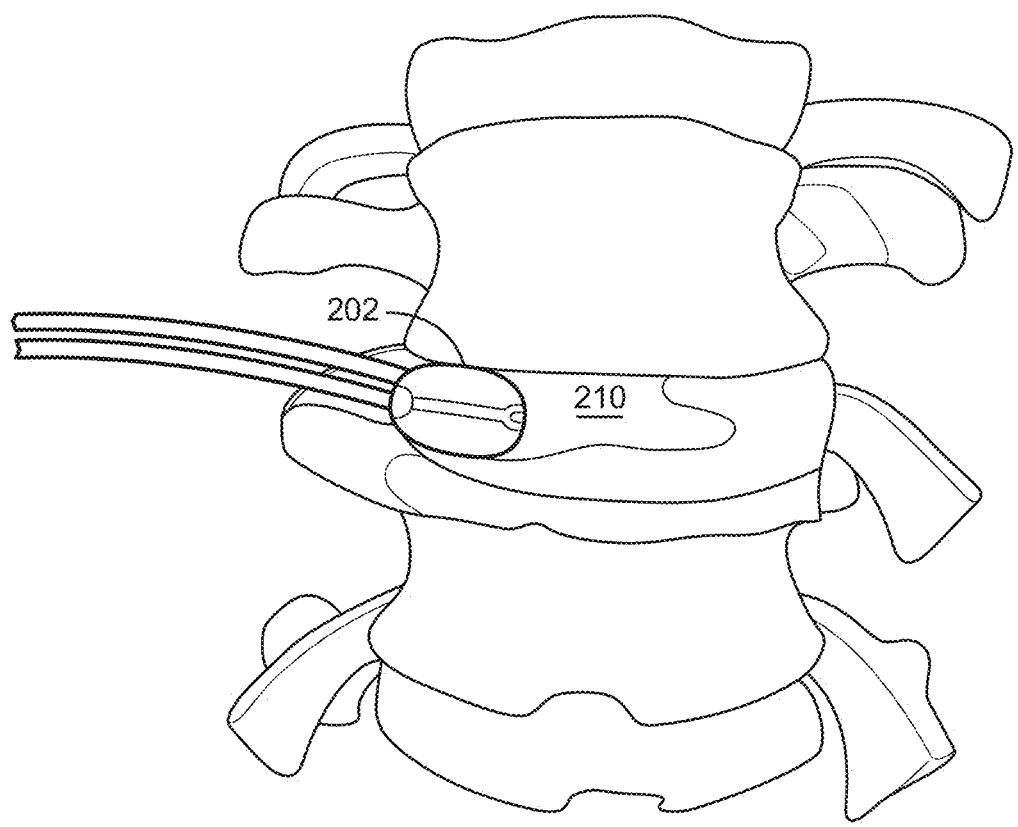

FIG. 27 shows the balloon 202 placed laterally inside the disc space 210, and the balloon 204 disposed posterior in the disc space. FIG. 28 shows balloon 204 when inflated by operation of the tool 212 to create flexion, and FIG. 29 shows balloon 202 when inflated to create lateral bending.

Figure 33:
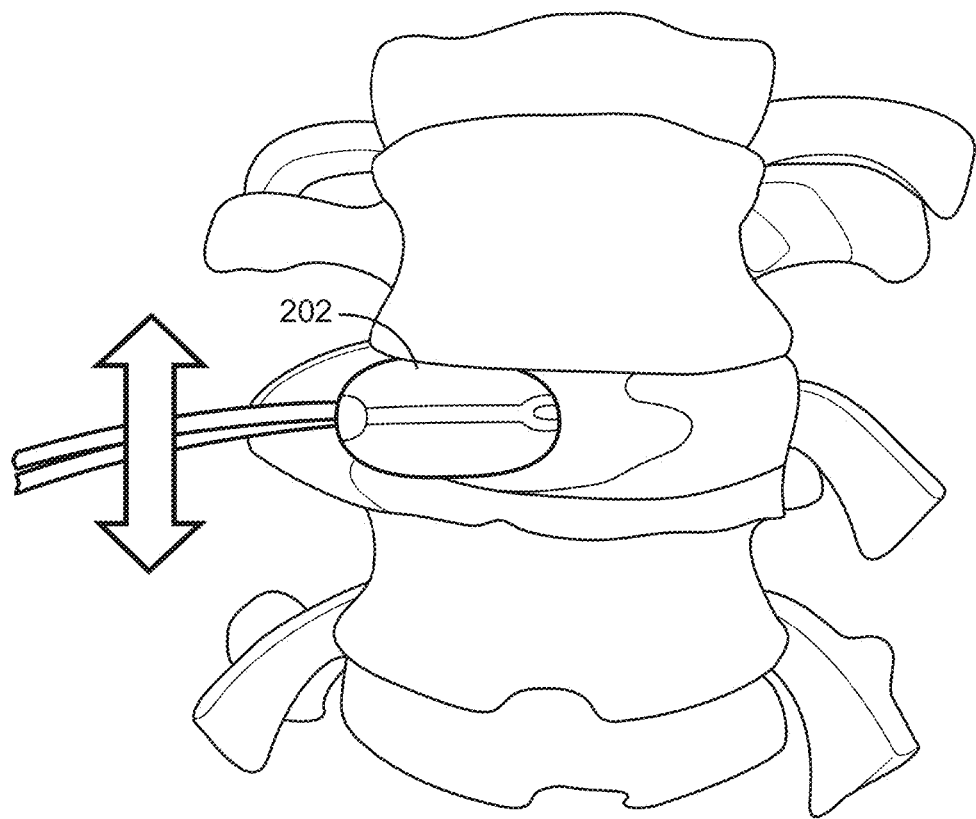
Figure 34:
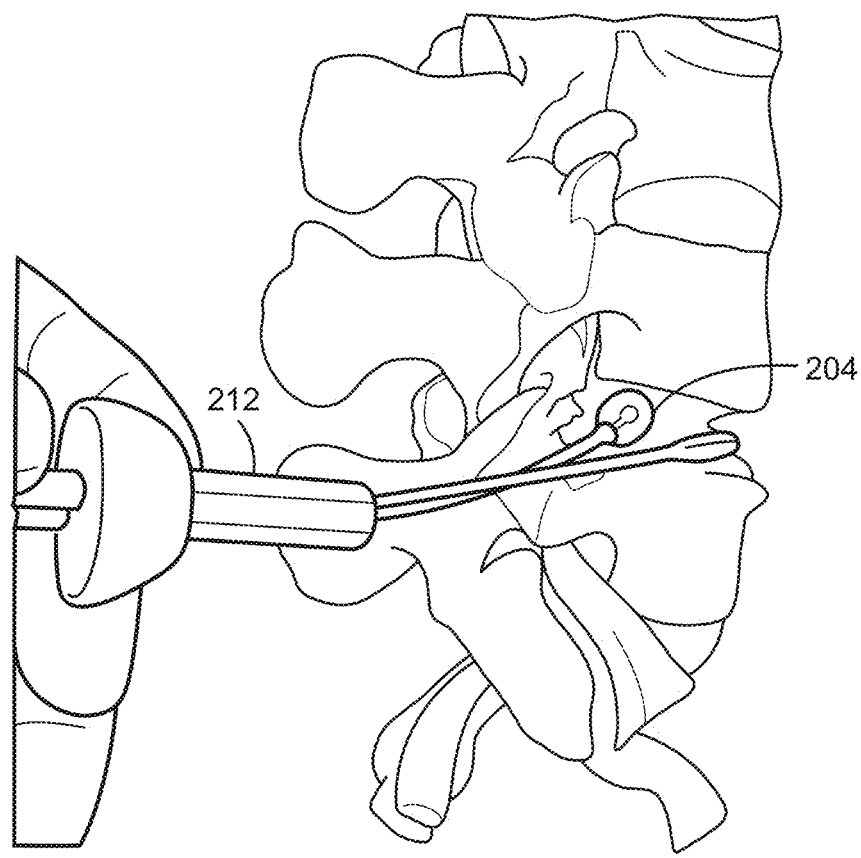
Figure 35:
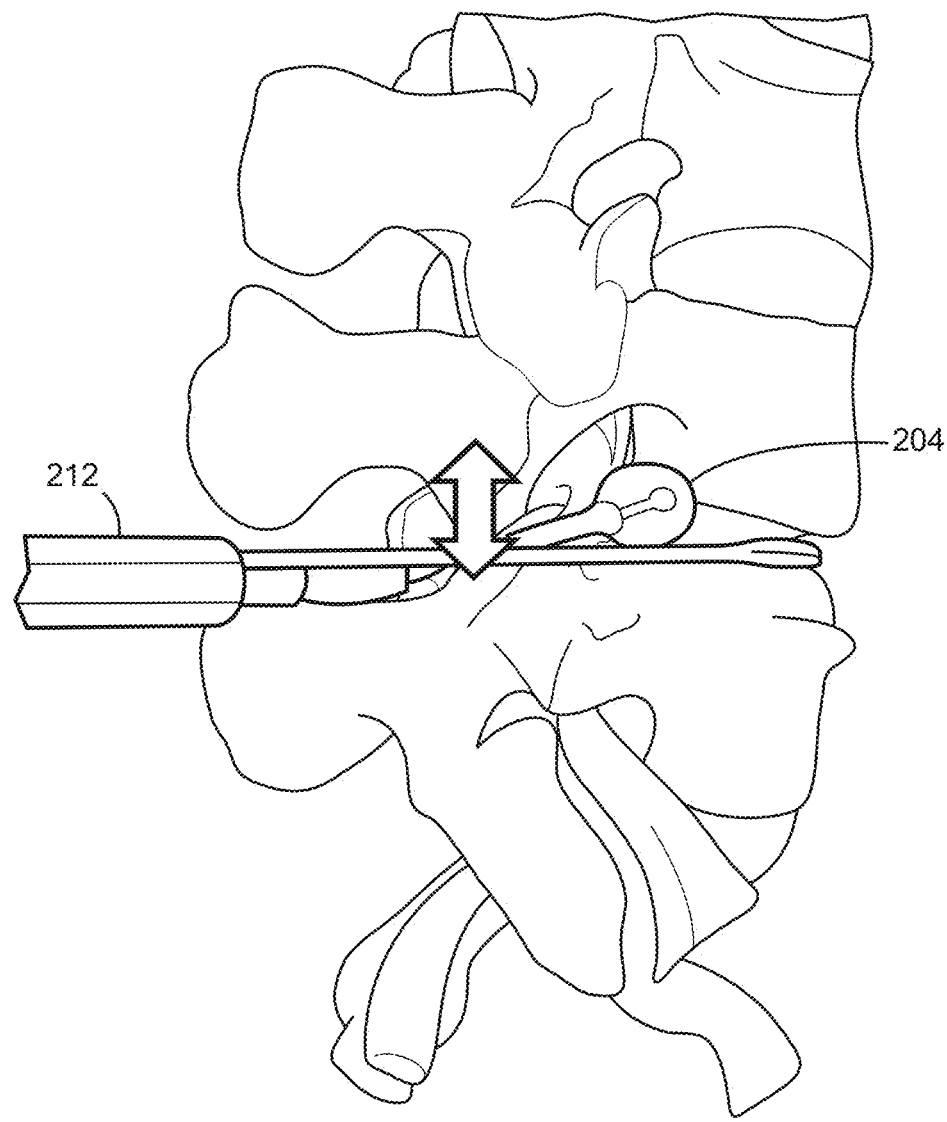

As seen in FIG. 33, increased inflation of the balloon 202 will produce more lateral bending of the spine. Balloon 202 is therefore inflated until the degree of lateral bending associated with the patient's POC is achieved. Further, as shown in FIG. 35, increased inflation of the balloon 204 will cause more forward flexion. Therefore, balloon 204 is inflated until the amount of forward flexion required for the patient's POC is achieved.

FIGS. 36 to 39 illustrate the use of multiple inflatable balloons in a prosthesis device 300 for applying forces on vertebral bodies 310, 312 spatially in three dimensions above and below a patient's disc space 314, according to the invention.

Figure 36:
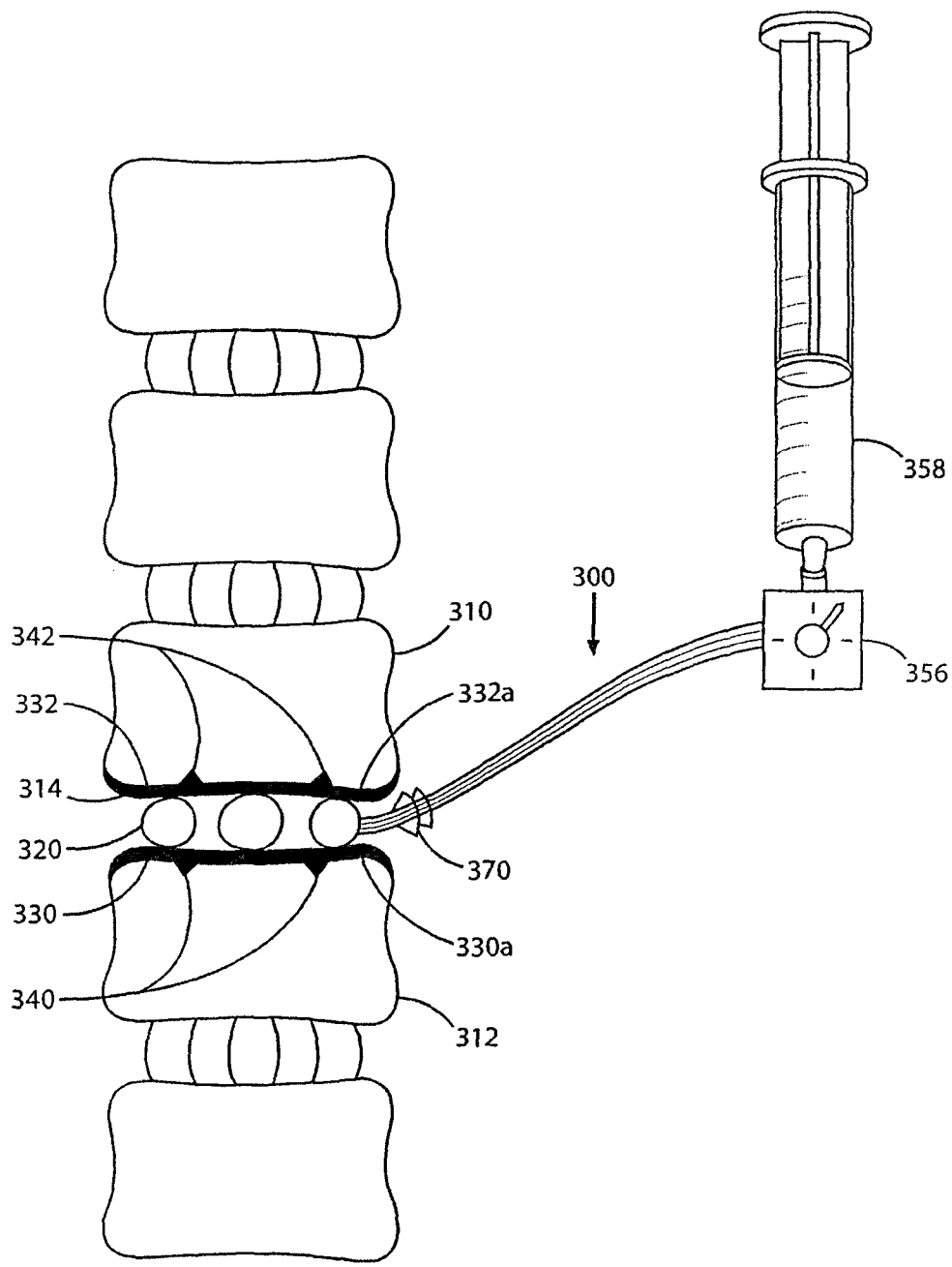
Figure 37:
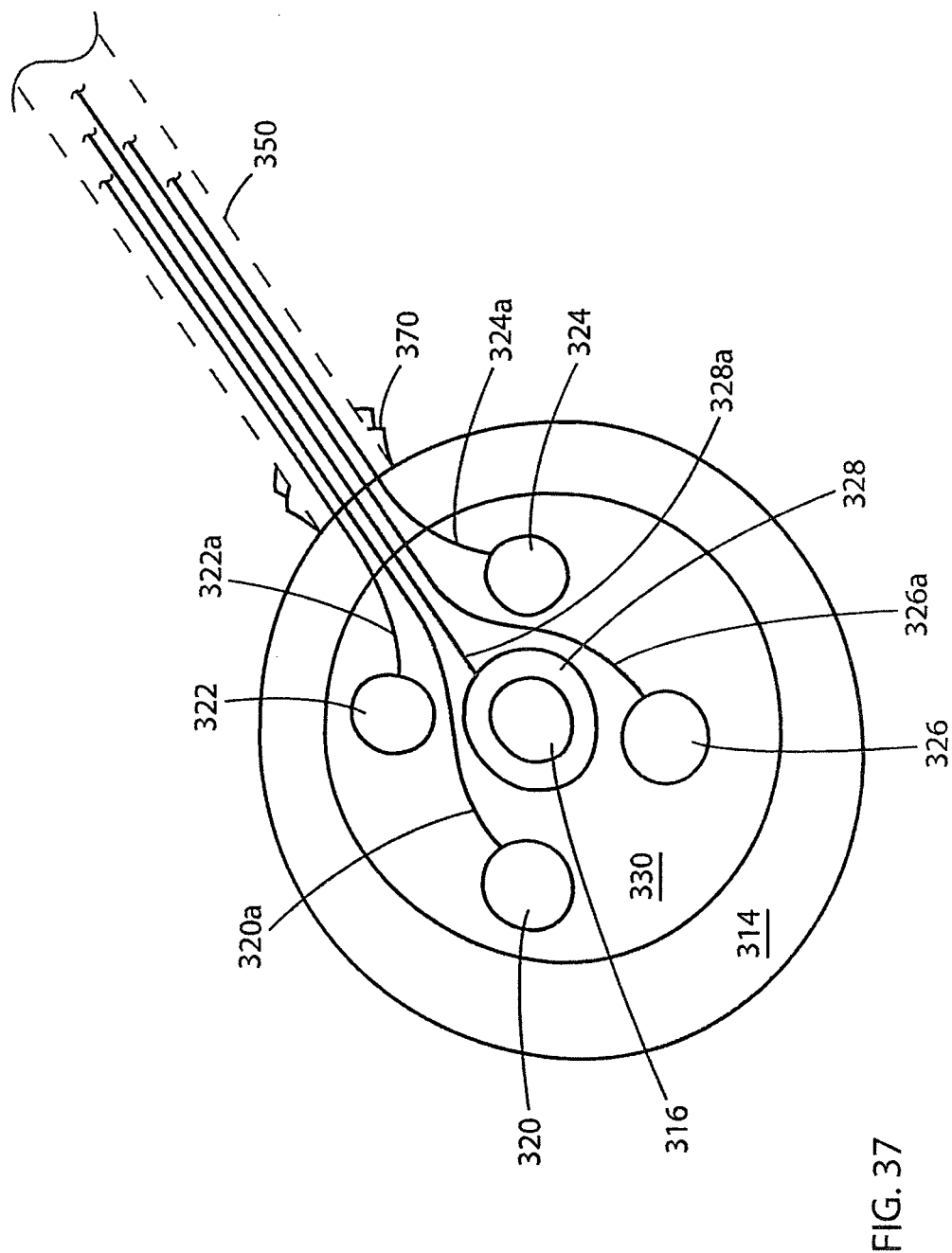
Figure 38:
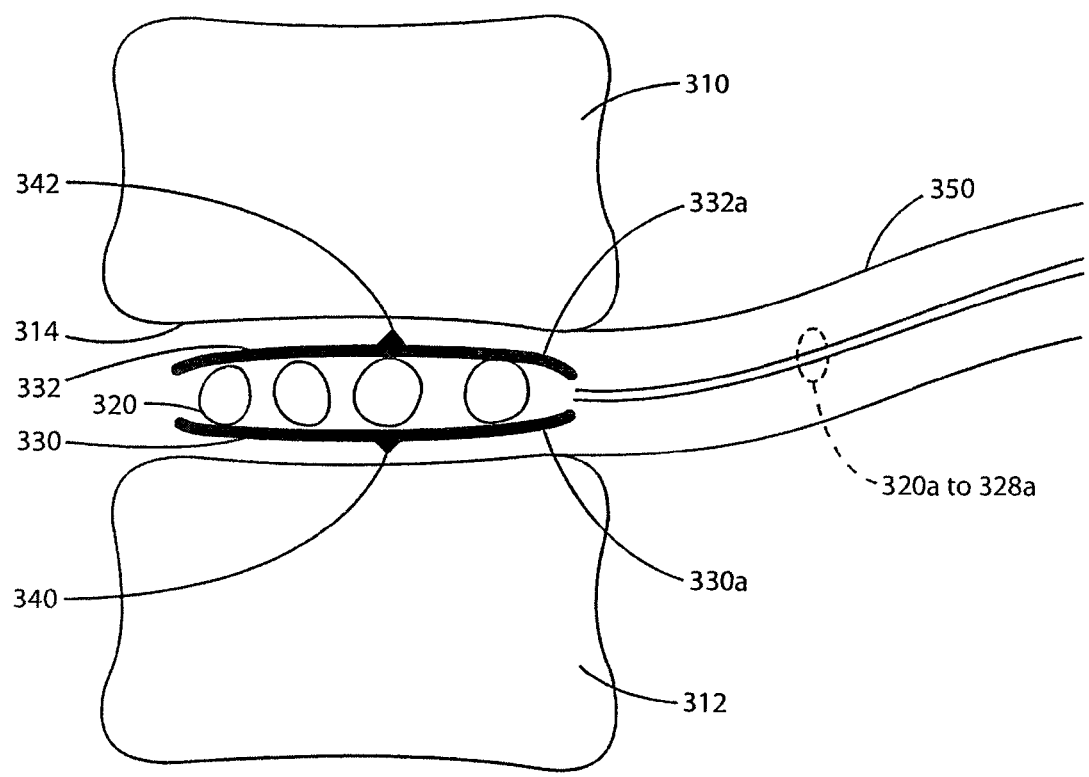
Figure 39:
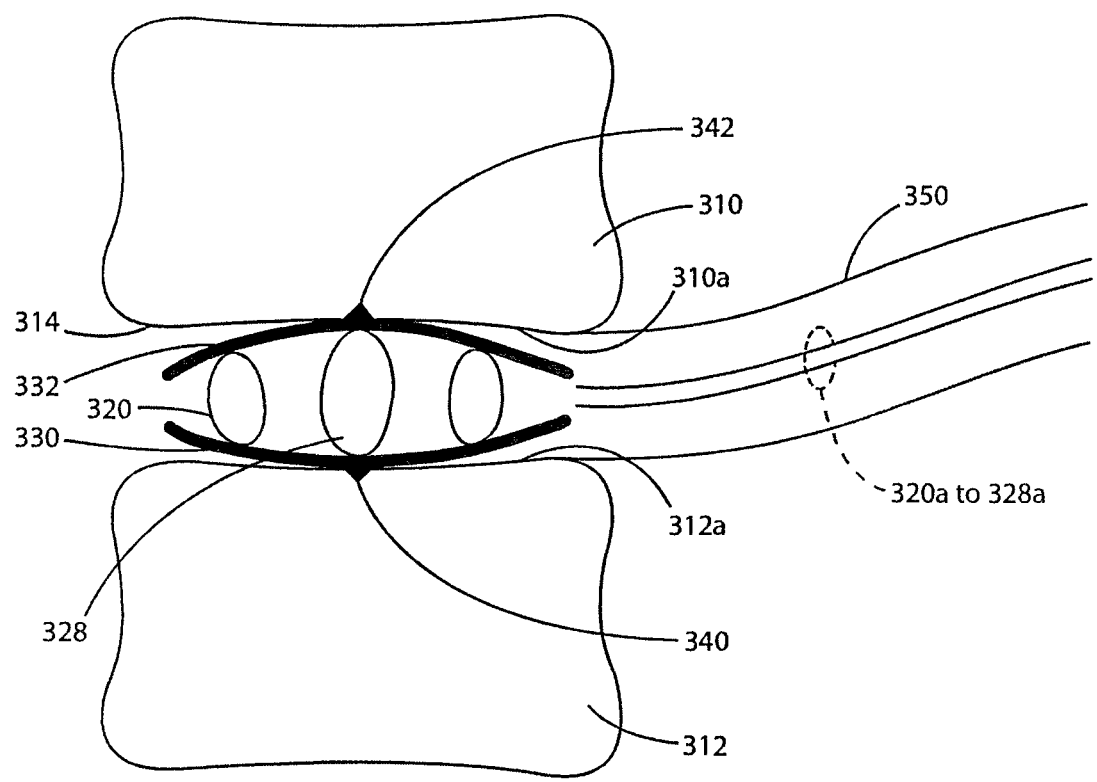

As seen in FIG. 37, a ring array of four inflatable balloons 320, 322, 324, 326, and an "anchor" balloon 328 that may be of toroidal shape when inflated, are adhered to and sandwiched between two flexible disk shaped plates or membranes 330, 332. The plates 330, 332 are formed, for example, from a flexible silastic or polyurethane-polycarbonate material. One or more sharp prongs or spikes 340, 342 project from the outwardly facing surfaces 330a, 332a of the plates in regions above and below the body of the anchor balloon 328. Each of the balloons 320 to 328 has an associated filling tube 320a to 328a through which the balloon may be inflated with a liquid substance or cement dispensed from an associated syringe or computer controlled infusion pump at a proximal end of the filling tube. Alternatively, as shown in FIG. 36, the proximal ends of the filling tubes 320a to 328a may be coupled to a filling tube selector 356 that is constructed and arranged in a known manner to enable a given substance contained in a syringe 358 to be channeled into selected ones of the tubes. The selector 356 is preferably also configured to receive syringes containing other substances to be channeled to selected filling tubes.

The plates 330, 332 are rolled with the deflated balloons 320 to 328 and their associated filling tubes 320a-328a so as to acquire a profile small enough to be passed axially through an outer tube 350, and inserted percutaneously into the patient's disc space 314 when exiting the distal end of the outer tube 350. To achieve a correct orientation, radiographic or visual markers may be incorporated on the balloons and/or other parts of the device 300 when inserted in the disc space. The balloons are then inflated selectively with air, water, or other liquid substance to allow flexibility, or with a cement to provide rigidity. The inflation process may also serve at least in part to unroll the plates 330, 332 with the balloons inside the disc space 314.

Once inserted in the patient's disc space 314, the anchor balloon 328 is preferably inflated first. As the latter expands, the outwardly projecting spikes 340, 342 on the plates 330, 332 are forced into vertebral end plates 310a, 312a above and below the disc space 314, while the deflated balloons 320 to 326 remain in place at determined positions in the disc space. Once the anchor balloon 328 is fully inflated, it forms an open central region 316 inside the disc space 314. If only one pair of spikes 340, 342 are each centrally located on a corresponding plate 330, 332 in axial alignment with one another, then the remaining deflated balloons 320 to 326 may be placed at desired positions inside the disc space by turning the plates about the axis of the spikes 340, 342.

The remaining balloons are inflated individually with air, water or other liquid substance, or cement through their filling tubes by operating the associated filling syringes or infusion pumps, or by using the filling tube selector 356 and an associated syringe 358. Each balloon is inflated by an amount sufficient to displace the vertebral end plates 310a, 312a above and below the balloon by a determined distance so that when all the balloons are inflated, the affected level of the patient's spine is urged into a position that achieves the patient's POC. Once the POC is achieved, the vertebral bodies 310, 312 are fused to one another by inserting cement, bone fragments, a bone substitute (e.g., BMP), or new biologic material into the open central region 316 formed by the anchor balloon 328. The central region 316 is preferably filled through a separate tube (not shown in the drawing), while the anchor balloon 328 remains inflated to ensure that the prongs 340, 342 will stay in place in the vertebral bodies 310, 312 and thereby prevent the balloons from migrating.

As mentioned, the proximal ends of the balloon filling tubes 320a to 328a may all be coupled to the filling tube selector 356 to allow a substance contained in a replaceable syringe 358 to be channeled through selected ones of the filling tubes. For example, water may be channeled into the filling tube of a selected balloon or balloons so as to move the vertebral bones of an awake patient to find his or her POC. Once the POC is achieved, an associated computer or processor may be configured to determine a quantity of bone cement needed to expand the same balloons to the same dimensions as when expanded by the water. The water is then expelled from the balloons, and the determined amount of cement is pumped into the balloons after coupling a different syringe to the selector 356. Different syringes or infusion pumps, each supplying a different inflation substance or cement, may also be permanently coupled to the filling tube selector 356 so that when a given syringe or pump is operated, its associated substance is channeled through the selected balloon filling tube.

While the foregoing represents preferred embodiments of the invention, it will be understood by those skilled in the art that various modifications, additions, and changes may be made without departing from the spirit and scope of the invention.

For example, in spine surgery, "biologics" are substances that can be injected into degenerative discs to restore and regenerate the disc to a healthy form. An implant or prosthesis determined and placed according to the invention may be used to hold a patient's spine in his or her POC, similar to a splint, until the biologic material is incorporated and disc healing has occurred. The implant may then be removed or dissolve over time, leaving a natural healthy disc. It is contemplated that the ability of biologics to reduce pain will be enhanced if the spine is held in the patient's POC while their body incorporates the biologic substance and heals. The material forming the implant device or prosthesis can therefore be made of a resorbable material that needs to last only long enough for the injected biologic substance to take hold.

Accordingly, the invention includes all such modifications, additions, and changes that are within the scope of the appended claims.

I claim:

1. A procedure for determining and placing spinal implants or prostheses, comprising:

measuring a spatial change in position of vertebrae at an affected level of a patient's spine from a first position at which the patient reports a greatest amount of pain known to originate from the affected level, to a second position at which the patient reports a least amount of pain originating from the affected level;

the measuring step including quantifying the spatial change in position in terms of one or more of flexion, extension, lateral bending, rotation, translation, compression, and distraction, and producing corresponding measurement data; and selecting, according to the produced measurement data, one or more spinal implants or prostheses that are configured to urge the affected level of the patient's spine toward the second position and away from the first position when the implants or prosthesis are applied to or placed in a disc space at the affected level.

2. A procedure according to claim 1, including providing a database, storing information in the database that corresponds to a number of different available spinal implants or prostheses, and the selecting step includes identifying the one or more implants or prostheses according to the information stored in the database.

3. A procedure according to claim 1, wherein the measuring step includes scanning the affected level of the patient's spine at the first position and at the second position, and producing corresponding image data.

4. A procedure according to claim 1, wherein the measuring step is performed by using an electrogoniomter or a torsiometer.

5. A procedure for determining and placing spinal implants or prostheses, comprising:

measuring a spatial change in position of vertebrae at an affected level of a patient's spine from a first position at which the patient reports a greatest amount of pain known to originate from the affected level, to a second position at which the patient reports a least amount of pain originating from the affected level;

the measuring step including quantifying the spatial change in position in terms of one or more of flexion, extension, lateral bending, rotation, translation, compression, and distraction, and producing corresponding measurement data; and selecting, according to the produced measurement data, an implant device of one or more inflatable balloons that are configured to urge the affected level of the patient's spine toward the second position and away from the first position when the device is placed in a disc space at the affected level and each balloon of the device is inflated a determined amount.

6. A procedure according to claim 5, wherein the measuring step includes scanning the affected level of the patient's spine at the first position and at the second position, and producing corresponding image data.

7. A procedure according to claim 5, wherein the measuring step is performed by using an electrogoniomter or a torsiometer.

8. A procedure according to claim 5, including inserting the implant device percutaneously into the disc space at the affected level.

9. A procedure according to claim 5, including dispensing a liquid substance or a cement for inflating the balloons of the implant device.

10. A procedure according to claim 5, including inserting a bone fixing material into an open central region in the disc space after the balloons of the implant device are inflated and vertebrae above and below the balloons are urged toward the second position at the affected level.

11. A procedure according to claim 10, including forming one of the balloons of the implant device as an anchor balloon so that when inflated, the anchor balloon defines the open central region in the disc space.

* * * * *